United States Patent [19]
Jarrett et al.

[11] Patent Number: 5,252,701
[45] Date of Patent: Oct. 12, 1993

[54] SEGMENTED ABSORBABLE COPOLYMER

[75] Inventors: Peter K. Jarrett, Southbury; Louis Rosati, Norwalk, both of Conn.; Donald J. Casey, Mars, Pa.

[73] Assignee: American Cyanamid Company, Stamford, Conn.

[21] Appl. No.: 548,801

[22] Filed: Jul. 6, 1990

[51] Int. Cl.$^5$ ............................................. C08L 71/02
[52] U.S. Cl. .................................... 528/354; 525/408; 525/411; 525/413; 525/415; 528/370
[58] Field of Search ................ 528/354, 370; 525/408, 525/403, 411, 413, 415

[56] References Cited

U.S. PATENT DOCUMENTS

| | | | |
|---|---|---|---|
| 4,243,775 | 1/1981 | Rosensaft et al. | 525/415 |
| 4,300,565 | 11/1981 | Rosensaft et al. | 128/333.5 |
| 4,891,263 | 1/1990 | Kotliar et al. | 428/225 |
| 4,916,193 | 4/1990 | Tang et al. | 525/413 |
| 4,916,207 | 4/1990 | Boyle et al. | 528/370 |
| 4,920,203 | 4/1990 | Tang et al. | 525/409 |
| 5,066,772 | 11/1991 | Tang et al. | 528/354 |
| 5,133,739 | 7/1992 | Bezwada et al. | 606/230 |

Primary Examiner—John Kight, III
Assistant Examiner—Shelley A. Dodson
Attorney, Agent, or Firm—Charles F. Costello, Jr.

[57] ABSTRACT

A copolymer comprising a bioabsorbable, segmented molecular architecture has been invented. The copolymer has at least two different ester linkages. The segmented molecular architecture comprises a plurality of fast transesterifying linkages. The fast transesterifying linkages have a segment length distribution of greater than 1.3. The segmented molecular architecture also comprises a plurality of slow transesterifying linkages. The following proviso is a material limitation to this invention: for the fast transesterifying linkages consisting essentially of glycolate linkages and the slow transesterifying linkages selected from the group consisting of trimethylene carbonate and caproate linkages, the segment length distribution of the fast transesterifying linkages is up to 2.0 and the number average segment length of the slow transesterifying linkages is greater than 2.5 linkages per segment. The copolymer is useful as an article of manufacture, for example a molding resin, surgical element and controlled release device.

40 Claims, 13 Drawing Sheets

SEGMENTED ABSORBABLE COPOLYMER

BACKGROUND OF THE INVENTION

This invention relates to a method of forming a bioabsorbable copolymer of specific and well defined molecular architecture, to the copolymer made by the method and to a medical or surgical device manufactured from the copolymer.

The following U.S. Pats. are considered to be background to the present invention: U.S. Pat. Nos. 3,023,192, 3,766,146, 3,268,487, 4,157,437, 4,157,921, 4,243,775, 4,246,904, 4,300,565, 4,429,080, 4,314,561, 4,605,730, 4,700,704, 4,643,191, 4,653,497, 4,716,203, and 4,838,267; and publication WO. 89/05664. These patents and the publication are incorporated herein by reference.

The term "molecular architecture," which is used in describing the present invention, refers to copolymers categorized as statistical (also called random), block or segmented (also called multi-block or random-block). Block copolymers can be diblocks, often symbolized as an AB block structure, or triblocks, often symbolized as an ABA block structure. Other block structures known in the art are "star-block" copolymers and "graft-block" copolymers. Segmented copolymers are sometimes symbolized as an $(AB)_n$ block structure. All of these architectures are well known to those skilled in polymer science.

The use of segmented copolymers in the preparation of medical devices is well known in the prior art. Interest in these materials stems from their excellent mechanical properties, which include combinations of their elastomeric behavior, high tensile strength, low stress relaxation (creep) and resistance to long term flexural fatigue failure. The excellent mechanical properties of these copolymers can be attributed to phase separation (domain formation) of the often noncrystalline "soft" segments and often crystalline "hard" segments contained within the copolymer chain. The soft segment contributes to the elastomeric behavior of the copolymer while the hard segment non-convalently crosslinks the copolymer and adds mechanical strength and toughness.

A vast quantity of literature exists which describes the relationship of molecular architectural parameters to polymer physical properties for non-absorbable copolymers. Background information on this field can be found in Allport, D.C., et al., "Property Structure Relationships in Polyurethane Block Copolymers," in *Block Copolymers*, Allport, D.C., and James, W.H., eds., John Wiley & Sons, 1973, pp 443-492 and in *Polymer Alloys: Blends, Blocks, Grafts and Interpenetrating Networks*, Klemper, D. and Frisch, K.C., eds., Plenum Press, 1979 and in *Polymer Alloys II: Blends, Blocks, Grafts and Interpenetrating Networks*, Klemper, D. and Frisch, K.C., eds., Plenum Press, 1979. These publications are incorporated herein by reference. The prior art in the field of non-absorbable polymers teaches one skilled in the art of the importance of molecular architecture in determining material physical properties. Examples of non-absorbable copolymeric materials having a segmented molecular architecture that have been used in medical applications are HYTREL (a DuPont polyester), PELLETHANE (an Upjohn polyurethane) and BIOMER (an Ethicon polyurethane), which are incorporated herein by reference.

The use of cyclic ester monomers in the preparation of block copolymers is known in the art. Investigators have used low temperature polymerication methods, often in solution, and exotic catalysts to avoid transesterification reactions to obtain a variety of block copolyesters which may be absorbable. Reference is made to the following relevant literature articles: Toyssio, P,H,, et al., J. Polym. Sci., 15, 1035-1041 (1977), Pong, X,D,, et al., J. Polym. Sci., Polym. Lett., 21, 593-600 (1983), Inoue, S., et al., Macromolecules, 17, 2217-2222 (1984) and Song, C. X. and Pong, X. D., Macromolecules, 17, 2764-2767 (1984). These publications are incorporated herein by reference. Such "living polymerization" methods, due to the need for organic solvents, are not desirable for producing medical goods, and are not advantageous for commercial scale applications. Also, these methods are not easily adaptable to the preparation of copolymers with a broad range of segment lengths within a single polymerization.

The concept of sequential addition copolymerization for copolymers of glycolide and lactide was first disclosed by Klootwijk in U.S. Pat. No. (hereafter "U.S.") 3,268,487. Specific examples of glycolide/lactide sequential addition copolymers were taught by okuzumi, et al. in U.S. Pat. No. 4,157,437 and U.S. Pat. No. 4,157,921. Further examples of glycolide/lactide, ε-caprolactone/glycolide and trimethylene carbonate (with a variety of comonomers) are taught by Rosensaft, et al., in U.S. Pat. No. 4,243,775 and U.S. Pat. No. 4,300,565. Still further specific examples of trimethylene carbonate/glycolide copolymers suitable for use as sutures are taught by Casey and Roby in U.S. Pat. No. 4,429,080. Finally, copolymers of ε-caprolactone and glycolide (U.S. Pat. No. 4,605,730 and U.S. Pat. No. 4,700,704); p-dioxanone and lactide (U.S. Pat. No. 4,643,191), p-dioxanone and glycolide (U.S. Pat. No. 4,653,497 and U.S. Pat. No. 4,838,267), ε-caprolactone and other monomers (U.S. Pat. No. 4,788,979), and lactide and trimethylene carbonate (WO 89/05664) have been synthesized. The U.S. Pat. No. 4,788,979 is incorporated herein by reference.

While these patents teach the preparation of block copolymers via a sequential route, the concept of preparing segmented copolymers from cyclic esters with control over both the average segment length *and* the distribution of segment lengths has not yet been addressed in the prior art. It is the object of this invention to prepare block and segmented copolymers with predictable molecular architectures having good control over the segment lengths and segment length distributions.

Such a copolymerization method results in copolymers with unexpected architectures. For example, since transesterification is known to occur in all esters, it is unexpected to prepare well defined block copolymers, that is block copolymers without the complication of transesterification reactions, of the A-B or $(A-B)_n$ type under commonly used melt copolymerization conditions. However, we have found that when cyclic ester monomers such as ε-caprolactone or trimethylene carbonate are employed in the first stage of the polymerization, well defined block copolymers are formed without the complications of reshuffling or scrambling reactions. It is to be understood that in this application the term "epsilon-caprolactone" will be described by using both the Greek letter for epsilon and the arabic letter "e". That is, in this application the terms "epsilon-caprolactone", "ϵ-caprolactone", and "e-caprolactone" are synonomous.

A second example of an unexpected result, is that addition of a minor amount of a second monomer (such as glycolide or lactide) to the ϵ-caprolactone or trimethylene carbonate in the first stage of the copolymerization followed by the addition of a 2nd stage comprised largely of the second comonomer, results in copolymers with segmented, or $(A-B)_n$, architectures with controllable and well-defined segment lengths. Such copolymers display markedly different physical properties as compared to corresponding random or block copolymers of similar composition.

Still further, by varying the polymerization time following the second stage addition, to times beyond full conversion of monomer to polymer, one can control the distribution of segment lengths. This occurs with no change in overall conversion or copolymer composition. Segment length distribution has also been found to have a marked effect on the physical and mechanical properties of the resulting copolymers. For a given composition as the segment length distribution narrows with polymerization time, properties such as melting point, and degree of crystallinity decline, and their related physical and mechanical properties change accordingly.

Still further, it is unexpected that increasing the concentration of monomer known to form "hard segments" results in copolymers with lower melting point and degree of crystallinity and greater flexibility. However, we have found that in the segmented copolymers of this invention, such an effect has been observed.

These materials may find use as absorbable medical or surgical devices where control over mechanical properties such as strength, stiffness and toughness is needed. Specific utility as a medical or surgical device includes, but is not limited to, a surgical suture and a controlled release device. Another utility of the copolymer of this invention may be as a surgical mesh or a tubular article, for example a vascular graft.

SUMMARY OF THE INVENTION

This invention relates to new and useful multiblock or block polymers and a process for producing bioabsorbable copolymers with predictable molecular architecture having specific segment lengths and distributions of segment lengths. The process can be used to prepare block copolymers (of the AB or ABA type) or segmented (also known as multiblock or random-block) copolymers of the $(AB)_n$ type.

The process is a two (or more) stage ring opening copolymerization using two (or more) cyclic ester monomers which form linkages in the copolymer with greatly different susceptibilities to transesterification. The process can be illustrated by describing the polymerization of a pair of monomers such as ϵ-caprolactone, which forms slow reacting (transesterifying) caproate linkages and glycolide, which forms fast reacting glycolate linkages when conventional tin based catalysts are employed.

The first stage (Stage I) of the copolymerization consists of a statistical copolymer which has a high content of the slower transesterifying (e.g. caproate) linkages and a low content of fast reacting (e.g. glycolate) linkages. This prepolymer forms a framework of segments consisting of runs of consecutive caproate linkages with interspersed short glycolate segments. The length and distribution of these segments depends on monomer feed composition, the reactivity ratios of the monomers and the degree of transesterification that occurs in this stage of the reaction. The framework, then, consists of segments with different reactivities for transesterification.

The second stage (Stage II) of the copolymerization consists of the addition of the fast reacting (e.g. glycolide) monomer and continuing the reaction for a specified length of time. The difference in transesterification reactivities of the two segments in the prepolymer preserves the caproate segments in the final copolymer. The second stage initially forms long glycolate segments, most likely at the ends of the Stage I prepolymer. Through transesterification, glycolate linkages from the initially long Stage II glycolate segments are gradually transferred into the shorter glycolate segments in the Stage I prepolymer. The result is a more narrow distribution of glycolate segment lengths. The resulting copolymer has a distribution of glycolate segment lengths. The resulting copolymer has a segmented (or multiblock) architecture, which is determined by the Stage I prepolymer framework, the final composition and the difference in transesterification rates. The distribution of segment lengths changes as a function of time after addition of the second stage. This distribution has a marked effect on material properties. In this way a wide range of material properties can be easily achieved by varying the reaction time for the second and any subsequent stages.

This mechanism is not necessarily limited to the caprolactone-glycolide pair. It has been shown that trimethylene carbonate shows similar behavior to caprolactone when copolymerized with glycolide, and l-lactide behaves similarly to glycolide when copolymerized with trimethylene carbonate. The observed differences in transesterification rates may be due to the interaction of the linkages with the catalyst. It is reasonable to believe that any combination of a linkage having a fast transesterification rate with a linkage having a slow transesterification rate can be used to prepare specific architectures in a copolymer of those linkages.

It is understood that the catalyst type and level of catalyst employed will affect both the relative polymerization and transesterification rates of the cyclic esters of the subject of this invention. By proper choice of both catalyst type and level, copolymers with specific architectures are prepared in a controllable manner and within a reasonable period of time. Catalysts such as stannous octoate or stannous chloride dihydrate are preferred. However, other catalysts known in the prior art, such as metal salt or metal oxide coordination catalysts, are within the scope of this invention.

The type of architectures that can be made utilizing this process can be AB diblock, ABA triblock, or segmented copolymers with wide or narrow segment length distributions. Diblocks and triblocks are made using monofunctional or difunctional initiators (alcohols) in the Stage I reaction and by using only the slow transesterification rate linkage to form a Stage I homopolymer. The Stage II linkages can only transesterify within the Stage II segment, preserving the diblock or triblock architecture.

A copolymer comprising a bioabsorbable, segmented molecular architecture has been invented. The copolymer has at least two different ester linkages. The segmented molecular architecture comprises a plurality of fast transesterifying linkages. The fast transesterifying linkages have a segment length distribution of greater than 1.3. The segmented molecular architecture also comprises a plurality of slow transesterifying linkages. The following proviso is a material limitation to this invention: for the fast transesterifying linkages consisting essentially of glycolate linkages and the slow transesterifying linkages selected from the group consisting of trimethylene carbonate and caproate linkages, the segment length distribution of the fast transesterifying linkages is up to 2.0 and the number average segment length of the slow transesterifying linkages is greater than 2.5 linkages per segment. The nomenclature for the various linkages which can be used in the copolymer is more fully described under the heading "Description of the Invention", below. The calculation of segment length distribution and number average segment length is fully described in Example 4, below. It is well known in the prior art that the inherent viscosity or molecular weight of a copolymer can be manipulated by the amount of initiator employed during the polymerization. For the copolymer described in this application, an inherent viscosity of greater than about 0.1 dL/g (concentration of 0.5 g/dL in a solvent, e.g. hexafluoroacetone sesquihydrate) is preferred. For an article of manufacture, e.g. a surgical suture, requiring an industry acceptable tensile (or other) strength value, an inherent viscosity of about 1.0 dL/g (0.5 g/dL in a solvent) or greater is preferred. For an article of manufacture, e.g. a controlled release device, where a strength value is not required, the copolymer can have an inherent viscosity of lower than about 1.0 dL/g (0.5 g/dL in a solvent). For those monomers not exemplified or claimed in this application, to determine if they will comprise a fast or a slow transesterifying linkage, the monomer of choice can be substituted for the trimethylene carbonate monomer of Example 5, below. After conducting the test of Example 5, if the block length is equal to or greater than 30, the final glycolate weight percent is 68, and the inherent viscosity is about 1.0 dL/g, then the monomer comprises a slow transesterifying linkage. An inherent viscosity substantially less than about 1.0 dL/g, means that the polymer formed is unstable at the test conditions.

In one embodiment of the copolymer the fast transesterifying linkages comprise lactate linkages. In another embodiment of the copolymer, the fast transesterifying linkages comprise glycolate linkages. In still another embodiment of the copolymer, the fast transesterifying linkages comprise lactate and glycolate linkages. In yet another embodiment of the copolymer, the slow transesterifying linkages are selected from the group consisting of trimethylene carbonate, caproate and dioxanone linkages. In a specific embodiment of the copolymer, the slow transesterifying linkages comprise trimethylone carbonate linkages. In another specific embodiment of the copolymer, the slow transesterifying linkages comprise caproate linkages.

Yet another embodiment of the copolymer is wherein the lactate linkages have a crystallinity of less than about 40 percent based on differential scanning calorimetry and a melting point of less than about 170° C. Still yet another embodiment of the copolymer is wherein the glycolate linkages have a crystallinity of less than about 30 percent based on differential scanning calorimetry and a melting point of less than about 215° C. In a more specific embodiment, the copolymer comprises a bioabsorbable, segmented molecular architecture having a plurality of lactate linkages. The segment length distribution of the lactate linkages is greater than 1.3, the crystallinity is less than about 40 percent based on differential scanning calorimetry and the melting point of the copolymer is less than about 170° C. The segmented molecular architecture also has a plurality of trimethylone carbonate linkages. As used throughout this application, the term "plurality" has a common English language definition, which essentially is: relating to or containing more than one.

An article of manufacture has also been invented. The article comprises a copolymer. The copolymer has a bioabsorbable, synthetic, segmented molecular architecture. The segmented molecular architecture comprises a plurality of fast transesterifying linkages selected from the group consisting of lactate and glycolate linkages, and mixtures thereof. The fast transesterifying linkages have a segment length distribution of greater than 1.3. The segmented molecular architecture also comprises a plurality of slow transesterifying linkages selected from the group consisting of trimethylene carbonate, caproate and dioxanone linkages. The following proviso is a material limitation to this invention: for the fast transesterifying linkages predominately comprising glycolate linkages and the slow transesterifying linkages selected from the group consisting of trimethylene carbonate and caproate linkages, the segment length distribution of the fast transesterifying linkages is up to 2.0 and the number average segment length of the slow transesterifying linkages is greater than 2.5 linkages per segment.

In one embodiment of the article the fast transesterifying linkages comprise lactate linkages. In another embodiment of the article the fast transesterifying linkages comprise glycolate linkages. In still another embodiment of the article, the fast transesterifying linkages comprise lactate and glycolate linkages. In yet another embodiment of the article, the slow transesterifying linkages are selected from the group consisting of trimethylene carbonate and caproate linkages.

In one embodiment, the article of manufacture comprises a molding resin. The molding resin comprises the copolymer. In another embodiment, the article comprises one or more extrusion pellets. In an alternative embodiment, the article comprises an extrusion resin. The extrusion pellets or resin comprises the copolymer. In yet another embodiment, the article comprises a film. The film comprises the copolymer.

The molding resin comprising the copolymer described in this application can be useful in a variety of industrial processes, e.g. blow, transfer or injection molding. Examples of products which can be manufactured from the molding resin described in this application include, but are not limited to, disposable eating implements and utensils, such as a plate and fork, respectively; disposable packaging, such as for fast food restaurants; and disposable containers, such as a bottle or a syringe.

The extrusion pellets or resin comprising the copolymer described in this application can be useful in a variety of industrial processes, e.g. dry spinning, and wet spinning including gel spinning. Examples of products which can be manufactured from the extrusion pellets or resin described in this application include, but are not limited to, a fiber, a film, and tubing including a porous hollow tube. The film can be useful in a variety of packaging materials.

In one other embodiment, the article of manufacture comprises a sterile surgical element. The sterile surgical element comprises the copolymer. For a general disclosure of medical (which includes the term "surgical") uses, see columns 4 and 5 in U.S. Pat. No. 4,135,622 issued Jan. 23, 1979, which is incorporated herein by reference. It is to be understood that in this application the terms "surgical" and "medical" are essentially synonymous, unless the description in this application is clearly limited to only one of these terms.

In a specific embodiment of the article, the sterile surgical element comprises at least one filament. The filament has a Young's modulus of from about 100,000 to 700,000 psi. In another specific embodiment, the article comprises a monofilament. In a more specific embodiment, the article comprises a suture or ligature. In a most specific embodiment, the article comprises a suture or ligature having a diameter of from about 0.02 to 0.70 mm; a Young's modulus of less than about 500,000 psi; a tensile strength of from about 50,000 to 150,000 psi; and an elongation to break of less than about 50 percent.

In yet another embodiment, the article comprises a controlled release device. The controlled release device comprises the copolymer. Examples of products which can be manufactured from the controlled release device include, but are not limited to, consumer products such as for personal hygiene. Examples of a personal hygiene product can be an antiperspirant formulation, or an odor control product. In a specific embodiment, the controlled release device comprises a plurality of microspheres. The microspheres of the invention can be dispersed in a pharmaceutically and pharmacologically acceptable liquid to obtain a slow release composition for parenteral administration.

In another specific embodiment, the article comprises a controlled release device in combination with a pharmaceutically or agronomically active ingredient. It is to be understood that the term "pharmaceutically active ingredient" is generic and includes both organically synthesized drugs and medicine, and genetically engineered materials. Examples of organically synthesized drugs and medicines can include, but are not limited to, a steroid, anticancer drug, cardiovascular medication, and an antibiotic. The agronomically active ingredient includes, but is not limited to, compositions of matter, and formulations thereof, which are useful to control parasites, such as parasitic moxidectin, and as a pesticide. To control parasites, the controlled release device in combination with the active ingredient, (for example parastiic moxidectin, provides a one dose treatment method for ruminant animals whereby said treated animals are protected for an extended period against infestation by nematodes, endoparasitic insects, ectoparasitic insects acarids and ruminant pastures are protected against contamination by the infective stages of these parasites that infest said animals. The controlled release device in combination with the active ingredient also provides a method for protecting ruminant animals for a prolonged period of time against infestation by nematodes, endo-and ectoparasitic insects and acarids, and decontaminating pastures to eliminate the infective stages of said parasites by orally administering to said ruminants a bolus, as described above, which continuously releases into the rumen of the treated animals, for a prolonged period of time, a therapeutically or prophylactically effective amount of the active ingredient, such as, for example, LL-F28249α, 23-(Q-methyloxime) LL-F28249α or a derivative thereof. Pesticidal compositions and processes for the preparation thereof are also within the scope of this invention. Each of the compositions contain a pesticidal agent, either alone or in a formulation, in combination with the copolymer described in this application. These compositions can provide an agronomically useful product which is characterized by extended residual activity (effectiveness).

In yet another specific embodiment, the article comprises a controlled release device in combination with a polypeptide or protein.

Biologically active proteins, peptides and polypeptides suitable for administration in the compositions of the invention include growth hormones, somatomedins, growth factors, and other biologically active fragments and derivatives thereof. Preferred proteins include bovine, ovine, equine, procine, avian, and human growth hormones; and is meant to encompass those which are of natural, synthetic, recombinant or biosynthetic origin. Examples of growth factors include a platlet-derived (alpha and beta), fibroblast, transforming, and insulin-like growth factor. Other proteins within the scope of this invention are cytokines, such as interferons, interleukins, various colony stimulating factors, and tumor necrosis factors. A specific embodiment of this invention is the incorporation of the biologically active protein peptide or polypeptide in the controlled release device comprising a plurality of microspheres.

A process for manufacturing a copolymer having a bioabsorbable segmented molecular architecture has also been invented. The process comprises employing sequential addition of at least two different cyclic ester monomers in at least two stages. The first cyclic ester monomer is selected from the group consisting of carbonates and lactones, and mixtures thereof. The second cyclic ester monomer is selected from the group consisting of lactides and mixtures thereof. The sequential addition comprises:

I. first polymerizing in a first stage at least the first cyclic ester monomer in the presence of a catalyst at a temperature of from about 160° to 220° C. to obtain a first polymer melt;

ii. adding at least the second cyclic ester monomer to the first polymer melt; and III. second copolymerizing in a second stage the first polymer melt with at least the second cyclic ester monomer to obtain a second copolymer melt.

The process also comprises transesterifying the second copolymer melt for up to about 5 hours at a temperature of greater than about 180° Centigrade.

In one embodiment of the process, the employing substep I comprises first polymerizing in the first stage from about 80 sole percent of said first cyclic ester monomer. The remaining mole percentage, if any, comprises the second cyclic ester monomer. In another embodiment of the process, the employing substep I comprises first polymerizing in the first stage up to about 90 mole percent of the first cyclic ester monomer. In still another embodiment of the process, the employing substep II comprises adding more than about 80 mole percent of the second cyclic ester monomer. The remaining mole percentage, if any comprises the first cyclic ester monomer. In a specific embodiment of the process, the employing substep II comprises adding 100 mole percent of the second cyclic ester monomer, Another process for manufacturing a copolymer having a bioabsorbable, segmented molecular architecture has been invented. The other process comprises employing sequential addition of at least two different cyclic ester monomers in three stages. The first cyclic ester monomer is selected from the group consisting of carbonates and lactones, and mixtures thereof. The second cyclic ester monomer is selected from the group consisting of lactides and mixtures thereof. The sequential addition comprises:

I. first polymerizing in a first stage at least the first cyclic ester monomer in the presence of a catalyst at a temperature of from about 160° to 220° C. to obtain a first polymer melt;

II. first adding at least the second cyclic ester monomer to the first polymer melt;

III. second copolymerizing in a second stage the first polymer melt with at least the second cyclic ester monomer to obtain a second copolymer melt;

IV. second adding at least the second cyclic ester monomer to the second copolymer melt; and V. third copolymerizing in a third stage the second copolymer melt with at least the second cyclic ester monomer to obtain a third copolymer melt.

The process also comprises transesterifying the third copolymer melt from up to about 5 hours at a temperature of greater than about 180° Centigrade.

In one embodiment of the process, the employing substep I comprises first polymerizing in the first stage from about 80 mole percent of the first cyclic ester monomer. The remaining mole percentage, if any, comprises the second cyclic ester monomer. In another embodiment of the process, the employing substep I comprises first polymerizing in the first stage up to about 90 mole percent of the first cyclic ester monomer. In still another embodiment of the process, the employing substeps II and/or IV comprise adding more than about 80 mole percent of the second cyclic ester monomer. The remaining mole percentage, if any, comprises the first cyclic ester monomer. In a specific embodiment of the process, the employing substeps II and/or IV comprise adding 100 mole percent of the second cyclic ester monomer.

In yet another embodiment of the process, the employing step comprises polymerizing in the presence of a metal coordination catalyst. In still yet another embodiment of the process, the employing step comprises polymerizing in the presence of an initiator. In a specific embodiment of the process, the initiator is selected from the group consisting of a monofunctional and polyfunctional alcohol.

DESCRIPTION OF THE INVENTION

Figure 1:
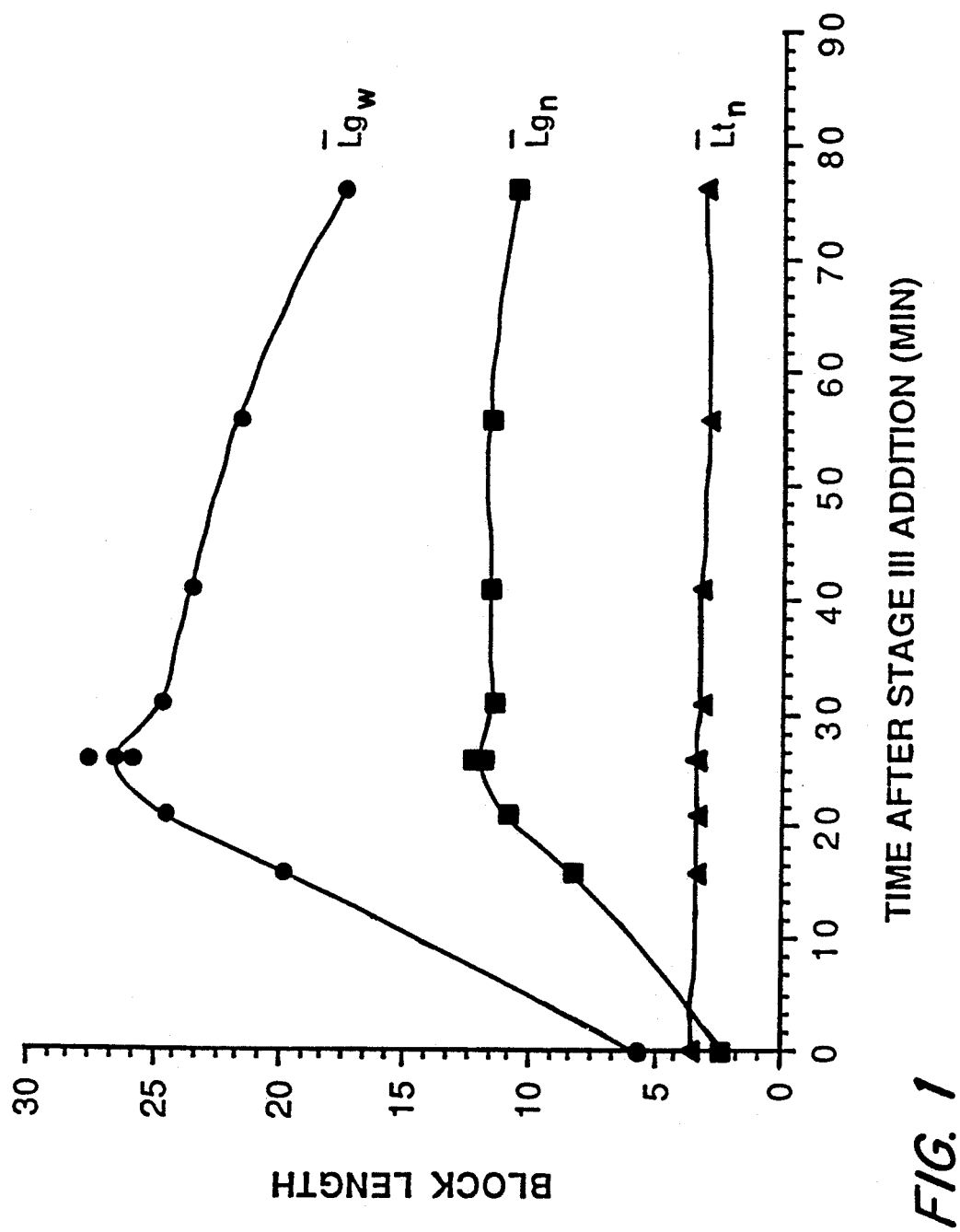
FIG. 1 shows in graphical form the various segment lengths as a function of polymerization time (after the stage III addition) for the polymers of Examples 8B to 8I.

It has now been found that sequential addition copolymerization of cyclic ester monomers can be utilized in conjunction with a selective transesterification phenomenon to crate bioabsorbable copolymer molecules with specific architectures. Such architectures can include block copolymers (of the AB or ABA type) or segmented (also known as multi-block or random-block) copolymers of the $(AB)_n$ type.

The sequential addition polymerization process of this invention is a two (or more) stage ring opening copolymerization using two (or more) cyclic eater monomers which form linkages in the copolymer with greatly different susceptibilities towards transesterification (a phenomenon we have termed "selective transesterification"). For example, such a pair of monomers is ε-caprolactons which forms slow reacting (transesterifying) caproate linkages and glycolide which forms fast reacting glycolate linkages when conventional tin catalysts are employed. Nomenclature and corresponding structures of a few relevant linkages are shown below.

| Linkage Nomenclature | Structure | Relative transesterification rate | Monomer |
|---|---|---|---|
| Caproate | $\pm O(CH_2)_5\overset{O}{\underset{\|}{C}}\pm$ | slow | ε-caprolactone |
| Glycolate | $\pm OCH_2\overset{O}{\underset{\|}{C}}\pm$ | fast | glycolide |

| Linkage Nomenclature | Structure | Relative transesterification rate | Monomer |
|---|---|---|---|
| Lactate | $\begin{array}{c}\phantom{O}CH_3\\\phantom{O}\mid\\\phantom{O}O\\\phantom{O}\parallel\\+OCHC+\end{array}$ | fast | lactide (d-, l-, dl-, and meso-, and mixtures thereof) |
| Trimethylene carbonate | $\begin{array}{c}O\\\parallel\\+OCH_2CH_2CH_2OC+\end{array}$ | slow | trimethylene carbonate |

Other parent monomers which may be useful in this process include: p-dioxanone, dioxepanone, deltavalerolactone, beta-butyrolactone, $\epsilon$-decalactone, 2,5-diketomorpholine, pivalolactone, alpha, alpha-diethylpropiolactone, 6,8-dioxabicyclo octane-7-one, ethylene carbonate, ethylene oxalate, 3-methyl-1,4-dioxane-2,5-dione, 3,3-dimethyl 1,4-dioxane-2,5-dione, substituted glycolides, substituted lactides. Other cyclic esters described in the art can also be employed within the scope of this invention. These monomers may be categorizable as to their susceptibility towards transesterification. Although not specifically exemplified, such a categorization would fit within the scope of this invention.

The first stage (Stage I) of the copolymerization consists of a statistical copolymer which has a high content of the slower transesterifying (e.g., caproate) linkages and a low content of fast reacting (e.g., glycolate) linkages. This prepolymer forms a framework of segments consisting of runs of consecutive caproate linkages with interspersed short glycolate segments. The length and distribution of these segments deepens on monomer feed composition, the reactivity ratios of the monomers and the degree of transesterification that occurs in this stage of the reaction. This framework, then, consists of segments with different reactivities for transesterification.

The second stage (Stage II) of the copolymerization consists of the addition of the faster reacting monomer (e.g. glycolide) and continuation of the reaction for a specified length of time. The difference in transesterification reactivities of the two segments in the prepolymer preserves the caproate segments in the final copolymer. The second stage initially forms long glycolate segments, most likely at the ends of the Stage I prepolymer. Through transesterification, glycolate linkages from the initially long Stage II glycolate segments are gradually transferred into the shorter glycolate segments in the Stage I prepolymer. The result is a more narrow distribution of glycolate segment lengths. The resulting copolymer has a segmented architecture, which is determined by the Stage I prepolymer framework, the final composition and the difference in transesterification rates. The distribution of segment lengths changes as a function of time after addition of the second stage. This distribution has a marked effect on material properties. In this way a wide range of material properties can be easily achieved by varying the reaction time for the second and subsequent stages.

This mechanism is not necessarily limited to the caprolactone-glycolide pair. It has been shown that trimethylone carbonate shows similar behavior to caprolactone when copolymerized with glycolide, and l-lactide behaves similarly to glycolide when copolymerized with trimethylene carbonate. The observed differences in transesterification rates may be due to the interaction of the linkages with the catalyst. While it is not our wish to be bound by theory we suspect that coordination of the growing polymer chain end/catalyst complex with linkages within the polymer chain is affected by the spacing (number of atoms) between carbonyl units, the polarity of the carbonyl units, and the micro-environmental effects of neighboring linkages. Linkages within the polymer chain which promote coordination with the catalyst complex would be expected to be more susceptible to undergo transesterification reactions. Such linkages are termed 'fast reacting' linkages. It is reasonable to believe that any combination of a linkage having a fast transesterification rate with a linkage having a slow transesterification rate (or "slow reacting linkage") can be used to prepare specific architectures in a copolymer of those linkages.

The above reasoning in the absence of experimental data (in some cases) permits the categorization of monomers, and the linkages formed from them, according to their predicted susceptibilities toward transesterification. The following monomers would be expected to form fast reacting linkages: Glycolide, lactide (l, d, dl or meso), 3-methyl-1.4-dioxane-2,5-dione, 3,3-diethyl-1,4-dioxan-2,5-dione, and other substituted "glycolide" type monomers.

The following monomers would be expected to form slow reacting linkages: 1,4-dioxan-2-one (hereafter called dioxanone linkages), 1,4-dioxepan-2-one, 1,5-dioxepan-2-one, delta-valerolactoner $\epsilon$-decalactone, pivalolactone, gamma-butyrolactone, ethylene carbonate, trimethylene carbonate, $\epsilon$-caprolactone, 6,8-dioxabicyclooetane-7-one. Other monomers known to copolymerize should be categorizable according to their reactivities. The reactivities of some of these monomers, however, are difficult to predict. These monomers include: 2,5-diketomorpholine, beta-butyrolactone, propiolactone and ethylene oxalate. Other cyclic esters described in the art can also be employed within the scope of this invention. The above categorizations are based upon theory, actual categorization of reactivities can only be accomplished experimentally. Such a categorization would be within the scope of this invention.

It is understood that the catalyst type and level of catalyst employed will affect both the relative polymerization and transesterification rates of the cyclic esters of the subject of this invention. By proper choice of both catalyst type and level, copolymers with specific architecture are prepared in a controllable manner and within a reasonable period of time. Catalysts such as stannous octoate or stannous chloride dihydrate are preferred, however other catalysts known in the prior art to be effective in the ring opening polymerization of cyclic esters are within the scope of this invention.

The types of architectures that can be made utilizing this process can be AB diblock, ABA triblock, or segmented copolymers with wide or narrow block length distributions. Diblocks and triblocks are made using monofunctional or difunctional initiators (alcohols) in the Stage I reaction and by using only the slow transesterification rate linkage to form a Stage I homopolymer. The Stage II linkages can only transesterify within the Stage II segment, preserving the diblock or triblock architecture.

It is generally preferred to conduct the sequential polymerization in a single reaction vessel, by sequentially adding the monomers thereto; however, if desired one or more of the stages can be polymerized in separate reaction vessels, finally combining the stages for transesterification in a single reaction vessel. Such a process would allow the use of acyclic polyester forming monomers for one or more of the stages. So long as the process of selective transesterification is utilized, this is within the scope of the present invention.

The concept of transesterification in aliphatic polyesters derived from cyclic monomers is known in the art. For example, Gnanou and Rempp, Macromol. Chem., 188, 2267–2275 (1987), have described the anionic polymerization of $\epsilon$-caprolactone in the presence of lithium alkoxides as being a living polymerization that is accompanied by simultaneous reshuffling. This article is incorporated herein by reference and is quoted in part as follows:

"If it [reshuffling] occurs between two different molecules, it is referred to as scrambling. It has no effect on the number of macromolecules nor on their number-average molecular weight, but it tends to broaden the MWD from a Poisson type to the most probable (or Schulz-Flory) distribution. Yet each macromolecule formed still carries one active site at the chain end."

"If reshuffling occurs intramolecularly it is called back-biting, and it results in the formation of cycles, the remaining linear macromolecules are of lower molecular weight, but they still carry an active site at the chain end."

The back-biting reaction is described in the article as follows:

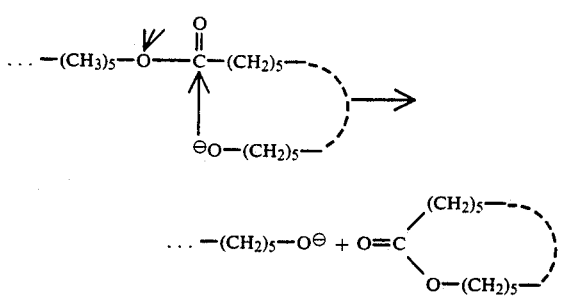

We have found that in copolymers certain ester linkages are susceptible to to varying degrees to transesterification (or reshuffling) reactions. When linkages of greatly different susceptibilities are present (such as caproate and glycolate), reshuffling or transesterification reactions occur primarily with the faster reacting (glycolate) linkages. Similar to the number average molecular weight of the homopolymer described by Gnanou and Rempp, in this instance reshuffling leads to little or no change in the number average segment lengths, as long as the composition is unchanged by these or other reactions. Similar to the molecular weight distribution effect described by Gnanou and Rempp, in this instance reshuffling tends to change the segment length distribution, in the direction of a Schultz-Flory or most probable distribution.

Utilizing these concepts we have found that a prepolymer (or Stage I polymer) can serve as a framework (or template) containing linkages with widely different susceptibility towards transesterification. The Stage I polymer contains predominately slow reacting linkages. Addition of a second stage (a second monomer addition) consisting of predominantly fast reacting linkage forming monomer results in:

1) polymerization of the Stage II monomer initiated by the Stage I/catalyst complex.
2) transesterification (reshuffling) consisting predominately of fast reacting linkage reactions leading to a narrowing of the fast reacting linkage segment length distribution over time.

After full conversion of the Stage II monomer to polymer, the number average segment lengths show little or no change as a consequence of the reshuffling reactions. As the reaction proceeds the architecture of the copolymer is determined by the following reaction variables:

1) Concentration of the fast reacting linkages in the Stage I copolymer: As the concentration of fast reacting linkages in the Stage I copolymer is increased, the transesterification reaction rate during the second (and subsequent) stages increases.
2) Catalyst type and concentration: The particle catalyst an level of catalyst employed determines the relative reactivities of the ester linkages, and the transesterification rate.
3) Reaction temperature and time: Reaction temperature and time will determine the rate and extent of the transesterification reactions and resulting segment length distribution.

The following Examples describe the best mode of practicing the claimed inventions which were known to the inventors at the time this application was filed.

EXAMPLES 1–3

Caprolactone-Glycolide Copolymers

Three copolymers were prepared from $\epsilon$-caprolactone and glycolide. In each case stannous octoate (0.01 mole % with respect to the total monomer concentration) and lauryl alcohol (0.4 mole % with respect to the total monomer concentration) were employed as the catalyst and initiator respectively. The polymerizations were conducted in a nitrogen purged, stirred reactor at 185° C. Monomers were charged into the reactor in one or two separate stages. Compositions are summarized in Table I below. Molecular weight was characterized by determination of inherent viscosity in CHCl$_3$ at 30° C. and a concentration of 0.5 g/dl (see Table I). Although all three copolymers have similar compositions, it is clear that the use of a two stage polymerization, in a proper order produces a copolymer (Ex. 1) with different physical properties than that produced by a single stage copolymerization, (Ex. 3). However, introduction of a fast transesterifying linkage such as glycolide in the first stage (Ex. 2) results in loss of the well defined block structure of Ex. 1 and leads to an amorphous material.

TABLE I

| Example # | Monomer Charge Ratios (ε-caprolactone/glycolide by weight) Stage I | Stage II | Final Composition Charged | Analyzed ($^1$H NMR) | IV (dL/g) (0.5 g/dL in CHCl$_3$) | Physical state |
|---|---|---|---|---|---|---|
| 1 | 100/0 | 50/50 | 70/30 | 68.7/31.3 | 0.54 | Crystalline |
| 2 | 50/50 | 100/0 | 70/30 | 67.9/32.1 | 0.56 | Amorphous |
| 3 | 70/30 | — | 70/30 | 68.4/31.6 | 0.60 | Amorphous |

EXAMPLE 4

Calculation of Average Segment Lengths

Kricheldorf et al (Macromolecules, 17, 2173-2181(1984), which is incorporated herein by reference, developed a method for measuring and calculating the number average segment lengths in statistical copolymers of glycolide and ε-caprolactone. This was done utilizing $^{13}$C-NMR to identify the four possible glycolate centered triad sequences i.e. GGG, CGG, GGC and CGC where G=glycolate and C=caproate.

The number average glycolate segment length ($Lg_n$) can be derived as follows:

For segments of length 1

$$L_i = 1$$

$$N_i = I_{CGC}$$

where I=integrated intensity of the triad of interest.

For segments of consecutive glycolate linkages of length greater than or equal to 2.

$$L_i = \frac{\text{total \# linkages}}{\text{total \# segments}} = \frac{I_{GGG} + I_{GGC} + I_{CGG}}{I_{CGG}}$$

$$N_i = I_{CGG} = I_{GGC}$$

Therefore $Lg_n = \frac{\Sigma N_i L_i}{\Sigma N_i}$ $$= \frac{I_{CGG}\left(\frac{I_{GGG} + I_{GGC} + I_{CGG}}{I_{CGG}}\right) + I_{CGC}(1)}{I_{CGG} + I_{CGC}}$$

$$= \frac{I_{GGG} + I_{GGC} + I_{CGG} + I_{CGC}}{I_{CGG} + I_{CGC}}$$

$$LG_n = \frac{I_{GGG} + I_{GGC}}{I_{CGG} + I_{CGC}} + 1$$

In a manner analogous to characterization of weight average molecular weight ($M_w$) we have defined a parameter ($Lg_w$) which uses NMR peak intensities to calculate a "weighted average segment length". This parameter is more sensitive to the longer glycolate segments. This parameter allows for the characterization of the effect of transesterification on glycolate segment length distribution. Current NMR instrumentation is limited in resolution to allow for quantification of glycolate centered triads. Determination and quantification of higher order sequences would provide greater accuracy in the calculation of $Lg_w$. The derivation of $Lg_w$ based on triad level resolution is as follows:

$$Lg_w = \frac{\Sigma N_i L_i^2}{\Sigma N_i L_i} = \frac{I_{CGG}\left(\frac{I_{GGG} + I_{GGC} + I_{CGG}}{I_{CGG}}\right)^2 + I_{CGC}(1)^2}{I_{CGG}\left(\frac{I_{GGG} + I_{GGC} + I_{CGG}}{I_{CGG}}\right) + I_{CGC}(1)}$$

$$= \frac{\frac{(I_{GGG} + I_{GGC} + I_{CGG})^2}{I_{CGG}} + I_{CGC}}{I_{GGG} + I_{GGC} + I_{CGG} + I_{CGC}}$$

Since current NMR instrumentation is only capable of resolving caproate sequences at the diad level, only the number average caproate segment length $Lc_n$ can be calculated. Kricheldorf's equations were used without modification.

$$Lc_n = \frac{I_{CC}}{I_{CG}} + 1 = \frac{I_{CC}}{I_{GC}} + 1$$

The segment length distribution $Lg_w/Lg_n$ is a unitless number calculated from NMR measurements.

The equations above are specific to one pair of fast and slow transesterifying linkages. It is understood that these equations also apply to other combinations of fast and slow transesterifying linkages, including combinations with more than one fast and/or more than one slow transesterifying linkages. These equations were used to characterize the copolymers prepared in Examples 1-3, the results are shown in Table II. Clearly the copolymer from Example 1, which contained a first stage comprising only caproate linkages, displayed higher number and weighted average glycolate and caproate segment lengths as compared to the polymers from Examples 2 and 3. The copolymer of Example 2, which was also polymerized via a sequential addition route closely resembled the copolymer from Example 3. This is due to the high concentration of rapidly transesterifying glycolate linkages in the Stage I prepolymer of Example 2.

TABLE II

| NMR Characterization | Polymer From | | |
|---|---|---|---|
| | Ex. 1 | Ex. 2 | Ex. 3 |
| WT. % CAPROLACTONE | 68.7 | 67.9 | 68.4 |
| $\overline{Lc}$ | 2.99 | 1.51 | 1.58 |
| $\overline{Lg_n}$ | 2.75 | 1.36 | 1.46 |
| $\overline{Lg_w}$ | 3.25 | 1.60 | 1.77 |

EXAMPLES 5-6

Block Copolymers of Glycolide and Trimethylene Carbonate

Two copolymers of glycolide and trimethylene carbonate were prepared using the sequential addition method. Both copolymers were made with 100% trimethylene carbonate (TMC) in the first stage and 100% glycolide (GLY) in subsequent stages. The overall composition of each copolymer was similar. The difference between the two copolymers was that one (Example 5) was polymerized in two stages whereas Example 6 was a three stage copolymer. Example 5 was prepared in the following manner:

| | Stage I |
|---|---|
| Time | 30 min |
| Temperature | 165° C. for 15 min. then increased to 180° C. over 15 min. |
| Charge: | TMC: 65.10 g |
| | $SnCl_2.2H_2O$: 4.09 mg |
| | Diethylene Glycol: 7.8 uL |
| | Stage II |
| Time | 2 hours |
| Temperature | 180° C. to 210° C. over 30 min |
| | 210° C. for 1.5 hours |
| Charge: | Gly 134.9 g |

Example 6 was prepared in the following manner:

| | Stage I |
|---|---|
| Time | 30 min |
| Temperature | 165° C. for 15 min. then increased to 180° C. over 15 min. |
| Charge | TMC: 65.10 g |
| | $SnCl_2.2H_2O$: 4.09 mg |
| | Diethylene Glycol: 7.8 uL |
| | Stage II |
| Time | 30 min |
| Temperature | 180° C. to 195° C. over 20 min. Hold at 195° C. for 10 min |
| Charge: | Gly 20.2 g |
| | Stage III |
| Time | 1 hour |
| Temperature | 195 to 215° C. over 15 min. Hold at 215° C. |
| Charge: | Gly 114.7 g |

The resulting copolymers were ground and placed in vacuum oven at 110° C.,<1 mm Hg overnight. Thermal analysis and $^{13}C$ NMR analysis were performed on the samples. The results of the analyses are shown in Table III.

TABLE III

| | Example 5 | Example 6 |
|---|---|---|
| Inherent Viscosity (0.5 g/dL) solutions in Hexafluoroacetone sesquihydrate) | 1.03 dL/g | 1.08 dL/g |
| Wt. % Gly ($^{13}C$ NMR) | 67.6 | 68.2 |
| Average Segment Lengths: | | |
| $Lt_n$ | 49.4 | 31.9 |
| $Lg_n$ | 38.9 | 39.1 |
| $Lg_w$ | 78.3 | 91.2 |
| Thermal Analysis (DSC) | | |
| Melting Point (°C.) | 214 | 215 |
| Glass transition (°C.) | −13, 36 | −13, 40 |

At these high values of segment length there is much scatter in the NMR data, therefore there are no significant differences in number average segment lengths, or segment length distribution. Thermal properties are also the same.

As evidenced by the high segment lengths of both copolymers (approaching the limit of instrument sensitivity) and the presence of two amorphous phases (two glass transition temperatures) the slowly transesterifying TMC homopolymer of Stage I minimizes reshuffling or scrambling reactions, preserving the block structure of the final copolymer.

COMPARATIVE EXAMPLE 7

Block Copolymers of Lactide and Trimethylene Carbonate

Copolymers of l-lactide and trimethylone carbonate (TMC) were prepared according to the following:

| | Stage I: |
|---|---|
| Time | 30 min |
| Temperature | 180° C. |
| Charge | TMC: 64.99 g |
| | Diethylene glycol: 16.38 uL |
| | Stannous octoate: 6.38 uL |
| | Stage II |
| Charge | l-lactide: 154.29 g |
| Ex 7A | |
| Time | 2 hrs. |
| Temperature | 190° C. |
| Ex 7B | |
| Time | 4 hrs. |
| Temperature | 190° C. |

The copolymers were dried in a vacuum oven at 110° C.,<1 mm Hg overnight. Analytical results for the copolymers are shown in Table IV.

These data indicate no significant differences in thermal properties between the two copolymers.

As evidenced by the high segment lengths (greater than the limit of instrument sensitivity) and the presence of two amorphous phases (two glass transition temperatures) the slowly transesterifying TMC homopolymer of Stage I minimizes reshuffling or scrambling reactions, preserving the block structure of the final copolymer.

The drop in inherent viscosity in Example 7B is believed to be due to thermolytic degradation of poly(TMC).

TABLE IV

| | Example 7A | Example 7B |
|---|---|---|
| Inherent Viscosity (0.5 g/dL in $CHCl_3$) | 1.68 | 1.01 |
| Wt. % lactide | 68.4 | 68.2 |
| Average Sequence Lengths: | | |
| $Lt_n$ | A | A |
| $Ll_n$ | A | A |
| $Ll_w$ | A | A |
| Thermal Analysis (DSC) | | |
| Melting Point (°C.) | 165 | 163 |
| Glass Transition (°C.) | −16, 54 | −10, 48 |

A) Block lengths infinite by NMR due to absence of peaks representing other than homopolymer triads.

EXAMPLE 8

Preparation of Segmented Copolymer of Glycolide and Trimethylene Carbonate - 3 Stage Copolymerization A copolymer of glycolide and trimethylene carbonate (TMC) was prepared according to the following:

Stage I

| Time | 3 hours |
|---|---|
| Temperature | 160° C. for 30 min, 160–180° C. over 20 min., hold at 180° C. |
| Charge | TMC: 81.23 g<br>Gly: 13.47 g<br>Diethylene glycol 21.66 uL<br>$SnCl_2 \cdot 2H_2O$: 5.87 mg |

Stage II

| Time | 15 min |
|---|---|
| Temperature | 180 to 195° C. over 10 min. |
| Charge | Gly 23.31 g |

Stage III

| Time | Variable after maximum melt viscosity |
|---|---|
| Temperature | 195 to 217° C. over 20 min hold at 217° C. |
| Charge | Gly: 131.99 g |

Small samples (<1 g) of Stage I and II copolymer were withdrawn for analysis. Samples of Stage III were taken at maximum melt viscosity and at intervals after maximum melt viscosity was achieved (see Table V). Copolymer samples were analyzed for inherent viscosity and average segment length was measured by NMR. Thermal properties were determined by DSC on samples which had been annealed in a vacuum oven at 110° C. and <1 mm $H_g$ overnight.

Figure 2:
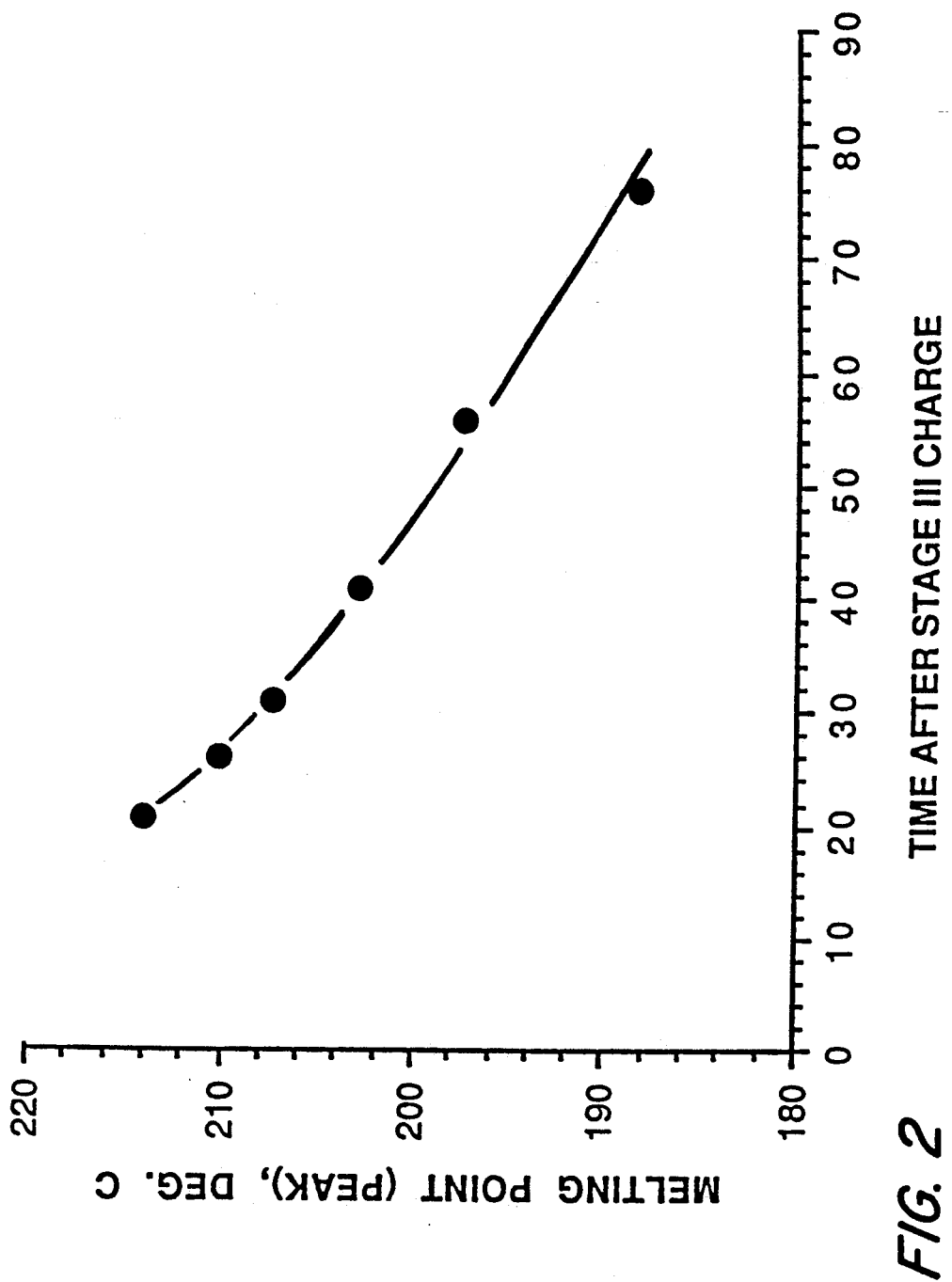
FIG. 2 shows in graphical form the melting points for the copolymers of Examples 8D to 8I, as a function of polymerization time, after the stage III addition.
Figure 3:
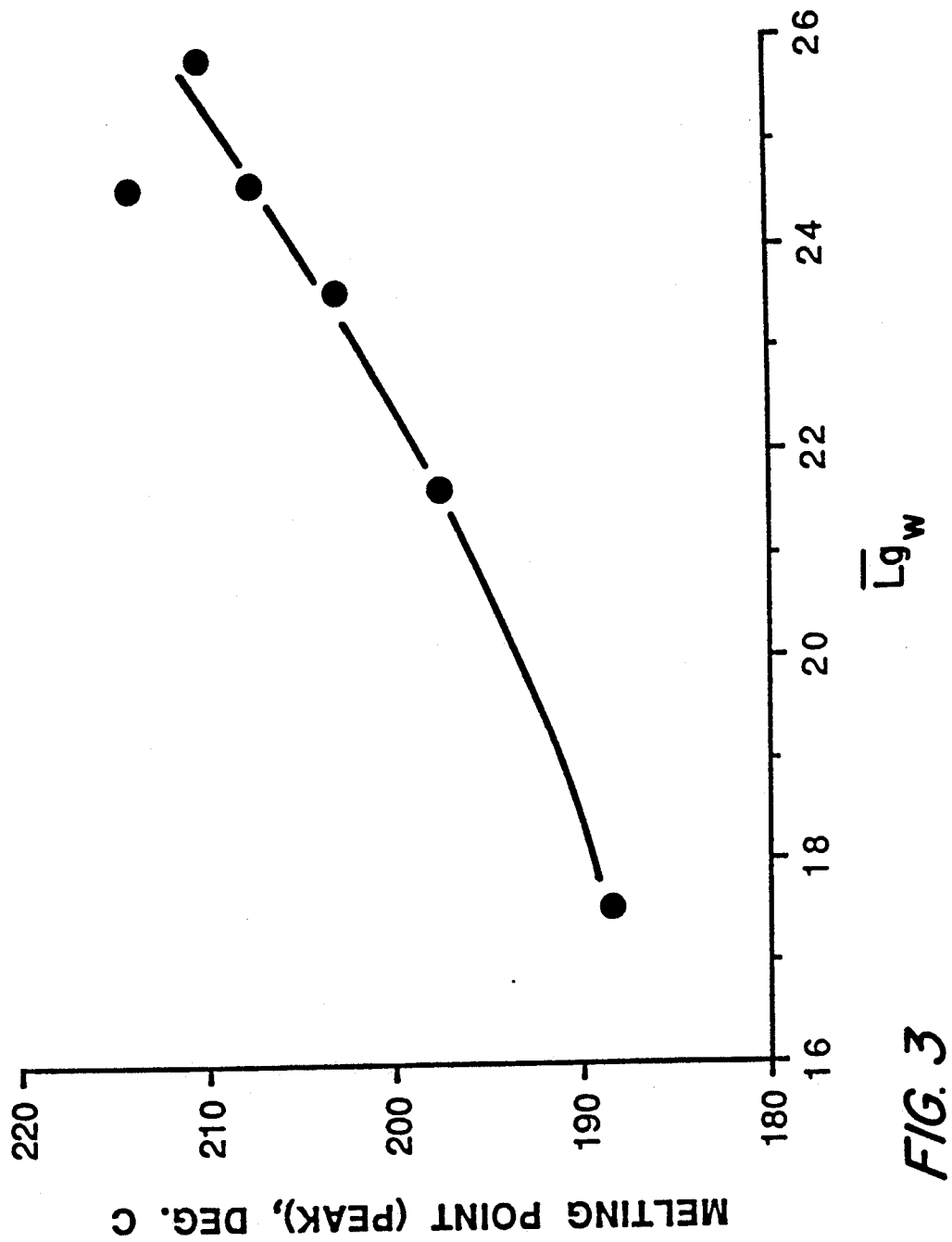
FIG. 3 shows in graphical form the correlation between melting point and $Lg_w$ for the copolymers of Examples 8D to 8I.

After full conversion of monomer to polymer $Lt_n$ and $Lg_n$ are relatively constant. However, $Lg_w$ decreases as a consequence of selective transesterification as shown in Table V and FIG. 1. In contrast to the lactide-TMC block copolymer of Example 7, the melting point decreases with time after the Stage III addition (see FIG. 2). Since the composition and number average segment lengths are constant the decrease in melting point must be a consequence of the narrowing segment length distribution. The relationship between melting point and weighted average glycolate segment length is shown in FIG. 3.

TABLE V (a)

| Example | Fraction | Time After Stage III Addition (min) | $IV^{(H)}$ | Composition Mole % Polyglycolide | Residual Monomer Mole % Glycolide | Residual Monomer Mole % TMC | Average Segment Lengths$^{(A)}$ $Lt_n$ | Average Segment Lengths$^{(A)}$ $Lg_n$ | Average Segment Lengths$^{(A)}$ $Lg_w$ |
|---|---|---|---|---|---|---|---|---|---|
| 8A | Stage I | — | — | 13.0 | 0 | 3.3 | 3.48 | 1.12 | 1.21 |
| 8B | Stage II | — | — | 25.1 | 0 | 0.3 | 3.48 | 2.29 | 5.62 |
| 8C | Stage III | 16 | 0.65 | 57.3 | 5.4 | 0.3 | 3.35 | 8.29 | 19.80 |
| 8D | " | 21 | 1.04 | 65.5 | 1.1 | 0.8 | 3.37 | 10.89 | 24.56 |
| 8E | " | 26 | 1.09 | 66.2 | 0.7 | 0.7 | 3.30 | 11.93 | 25.81 |
| 8F | " | 31 | 1.08 | 67.0 | 0.6 | 0.7 | 3.21 | 11.50 | 24.60 |
| 8G | " | 41 | 0.98 | 66.5 | 0.5 | 0.3 | 3.14 | 11.63 | 23.54 |
| 8H | " | 56 | 0.96 | 66.0 | 0.9 | 0.5 | 2.90 | 11.64 | 21.66 |
| 8I | " | 76 | 0.82 | 66.4 | 0.7 | 0.8 | 3.09 | 10.52 | 17.53 |

Explanation of footnotes are in Table V (b).

TABLE V (b)

| Example | Fraction | Thermal Properties$^{(B)}$ $Tg^{(C)}$ | Thermal Properties$^{(B)}$ $Tm^{(D)}$ | $\Delta H$ (cal/g)$^{(E)}$ Total | $\Delta Hf^{(F)}$ High Melting | Cloud Point$^{(G)}$ (uL DMSO) |
|---|---|---|---|---|---|---|
| 8A | Stage I | — | — | — | — | — |
| 8B | Stage II | — | — | — | — | — |
| 8C | Stage III | — | — | — | — | 380 |
| 8D | " | 11.3 | 214.0 | 12.05 | 12.07 | 430 |
| 8E | " | 16.7 | 210.1 | 12.10 | 11.34 | 440 |
| 8F | " | 12.3 | 207.4 | 12.21 | 11.24 | 430 |
| 8G | " | 14.8 | 202.9 | 11.98 | 10.90 | 430 |
| 8H | " | 12.0 | 197.5 | 11.42 | 10.19 | 430 |
| 8I | " | 14.2 | 188.4 | 11.60 | 9.71 | 460 |

$^{(A)}$Determined on as made copolymers
$^{(B)}$Determined on samples annealed at 110° C., <1 $mmH_g$ overnight
$^{(C)}$Mid-point of transition
$^{(D)}$Peak Maximum
$^{(E)}$Measured over entire endotherm region
$^{(F)}$Measured over main high melting endotherm only
$^{(G)}$5 mg copolymer dissolved in Hexafluoro-2-propanol (2 mL). Titrated with DMSO in 10 uL increments. Cloud point taken as volume of DMSO required to produce persistent haze in well stirred solutions.

EXAMPLE 9

Preparation of Segmented Copolymer of Glycolide And Trimethylene Carbonate-2 Stage Copolymerization A copolymer of glycolide and trimethylene carbonate (TMC) was prepared according to the following:

Stage I

| Time | 2½ hours |
|---|---|
| Temperature | 160° C. for 55 min., Raised to 180° C. over 13 min. Held at 180° C. for 1 hour 22 min |
| Charge | TMC: 81.23 g<br>Gly: 13.47 g<br>Diethylene Glycol: 21.66 uL<br>$SnCl_2 \cdot 2H_2O$ 5.87 mg |

Stage II

| Time | Variable after maximum melt viscosity |
|---|---|
| Temperature | 180° C. to 220° C. over 30 min. Held at 220° C. |
| Charge | Gly: 155.30 g |

A small sample of the Stage I copolymer was withdrawn for analysis. Samples of Stage II copolymer were taken (see Table VI) and were analyzed for inherent viscosity and average segment length was measured by NMR. Thermal properties were determined by DSC on samples which had been annealed in a vacuum oven at 110° C. and <1 mm Hg overnight.

Figure 4:
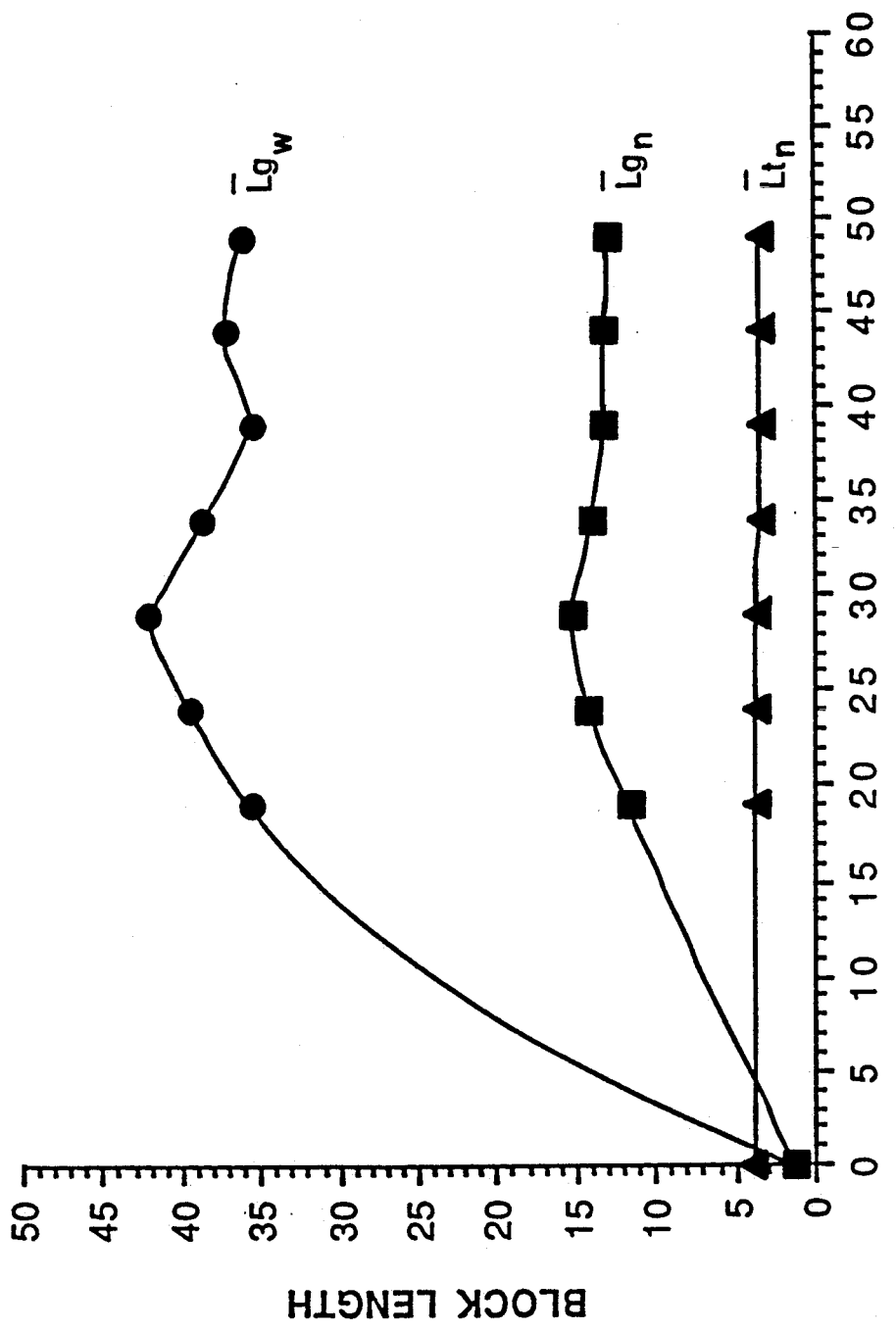
FIG. 4 shows in graphical form the various segment lengths as a function of polymerization time (after the stage II addition) for the copolymers of Examples 9B to 9H.
Figure 5:
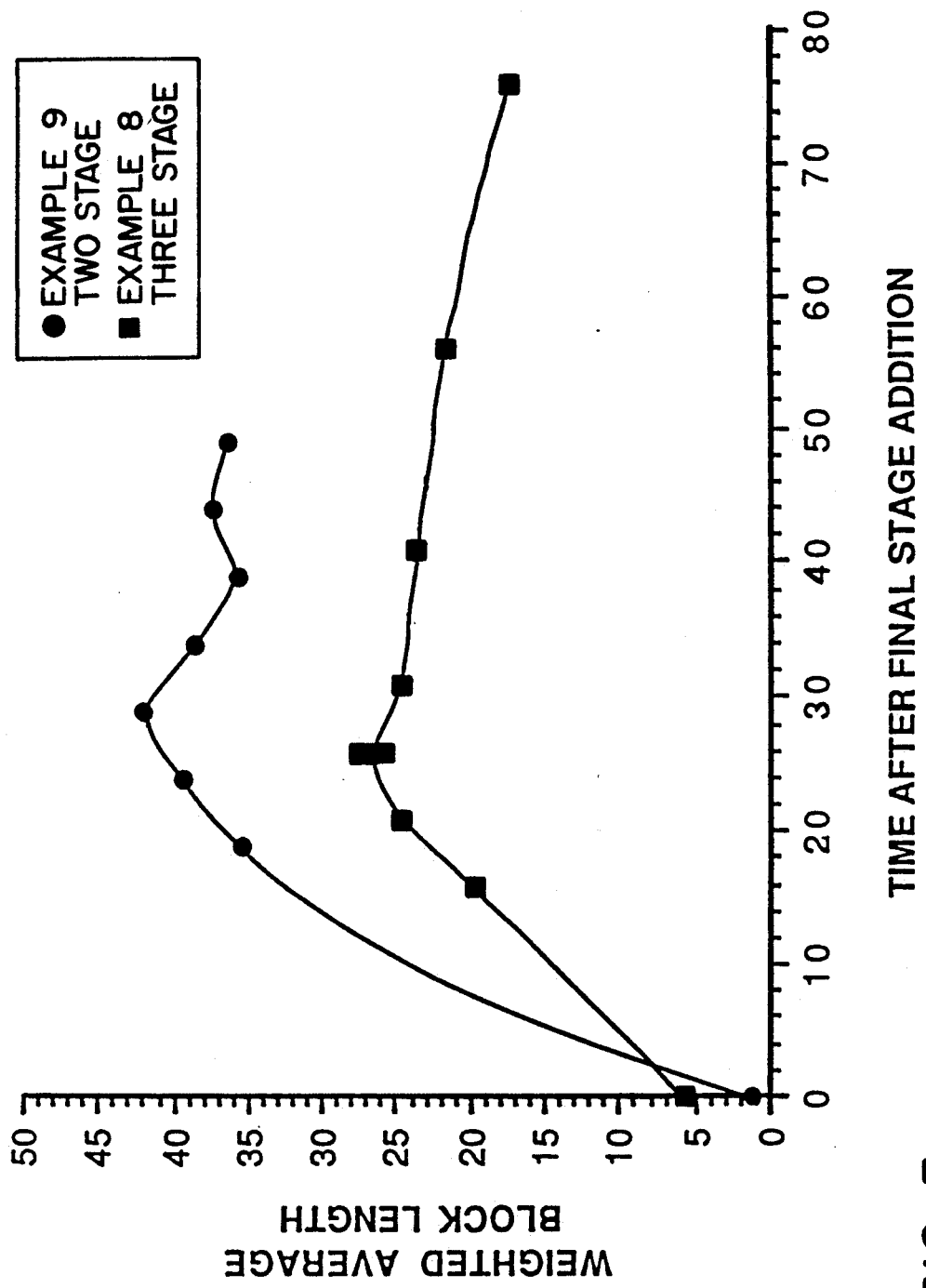
FIG. 5 shows in graphical form a comparison of the weighted average glycolate segment length ($Lg_w$) for the copolymers of Examples 8 and 9.

After full conversion of monomer to polymer both $Lt_n$ and $Lg_n$ are relatively constant. However, $Lg_w$ decreases as a consequence of selective transesterification as shown in Table VI and FIG. 4. Values of $Lg_n$ and $Lt_n$ are similar to those measured for the three stage copolymer of Example 8. In contrast to the copolymer of Example 8, the weighted average segment length $Lg_w$ of the currently exemplified two stage copolymer is considerably higher (FIG. 5). This difference between two and three stage copolymers also differs from the copolymers of Example 5 and Example 6, which showed no property differences when polymerized in either two or three stages.

Figure 6:
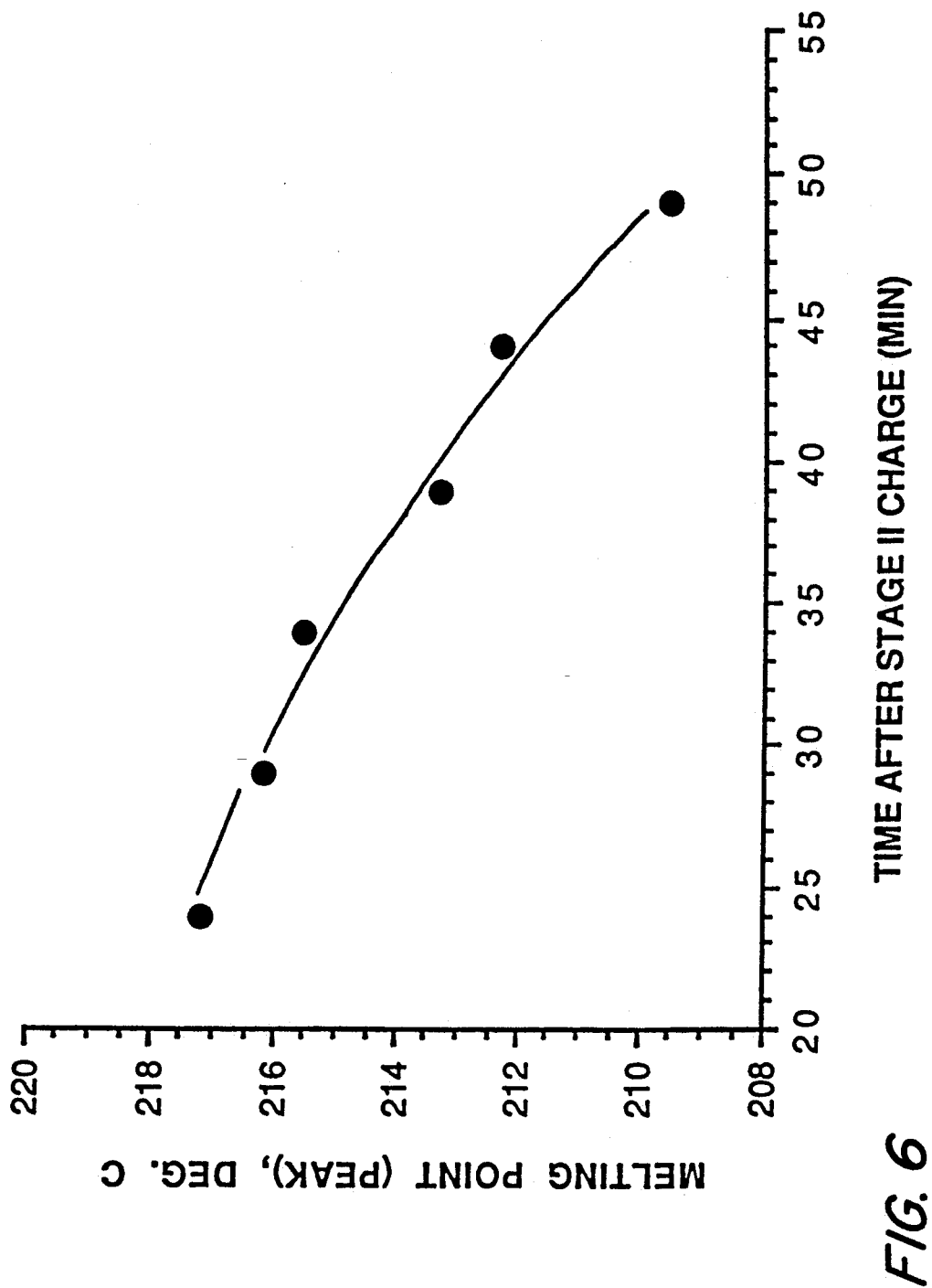
FIG. 6 shows in graphical form the melting point as a function of polymerization time (after the stage II addition) for the copolymers of Example 9C to 9H.

Higher values of $Lg_w$ for the two stage copolymer (as compared to the 3 stage copolymer of Example 8) results in differences in physical properties. This is apparent in the melting point data as plotted in FIG. 6 (as compared to the melting point data for Example 8 shown in FIG. 2), although the same trend of melting point decrease with time is apparent. In addition the large segment length distribution of the early time fractions (Example 9C-9F) is responsible for the formation of two distinct amorphous phases as evidenced by two glass transition temperatures. This behavior is similar to that noted for the block copolymers of Example 5 and Example 6. As polymerization time increased and transesterification was allowed to continue (Example 9G and 9H) the morphology changed, leading to a single amorphous phase (one glass transition temperature) similar to the copolymer of Example 8.

Figure 7:
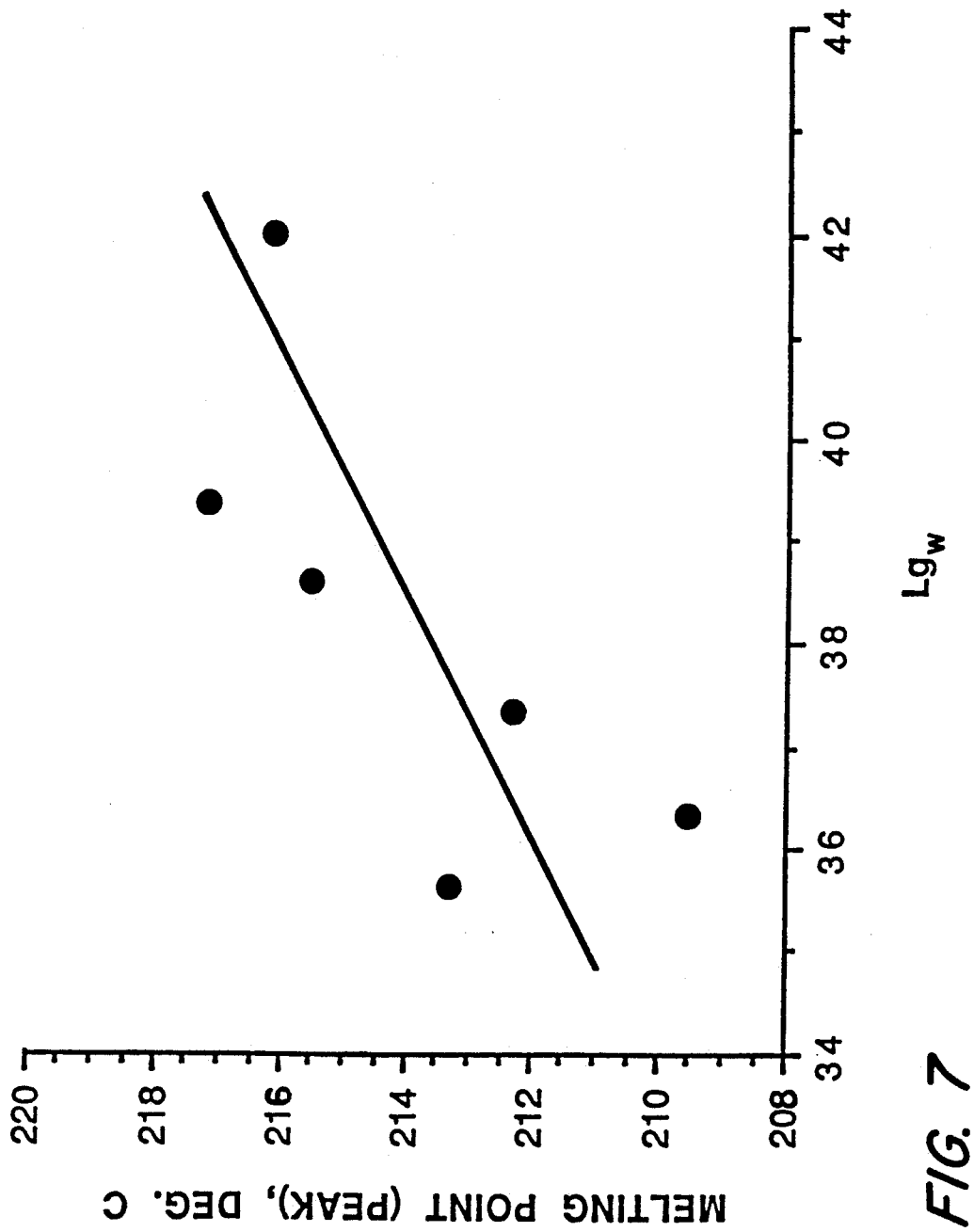
FIG. 7 shows in graphical form the correlation between melting point and $Lg_w$ for the copolymers of Examples 9C to 9H.

Also, as noted in Example 8 a relationship exists between $Lg_w$ and melting point (FIG. 7).

EXAMPLE 10

Preparation of Segmented Copolymers of Glycolide And Trimethylene Carbonate - 2 Stage Copolymerization - Stannous Octoate Catalyst A copolymer of Glycolide(Glyc) and Trimethylene Carbonate (TMC) was prepared according to the following:

|  | Stage I |
|---|---|
| Time: | 2 Hours 15 min |
| Temperature | 160° C. for 40 min |
|  | 160 to 180° C. over 15 min |
|  | Held at 180° C. |
| Charge: | TMC: 81.23 g |
|  | Gly: 13.47 g |
|  | Diethylene Glycol 21.38 uL |
|  | Stannous octoate 7.29 uL |
|  | Stage II |
| Time: | Variable after maximum melt viscosity |
| Temperature | 180 to 220° C. over 25 min |
|  | Held at 220° C. |
| Charge: | Glycolide 155.30 g |

A small sample of Stage I copolymer was withdrawn for analysis. Samples of Stage II copolymer were withdrawn at maximum melt viscosity and at varying time periods after maximum melt viscosity was achieved (see Table VII). Copolymer fractions were analyzed for inherent viscosity and average segment lengths were measured by NMR.

After full conversion of monomer to polymer both

TABLE VI (a)

| Ex. | Fraction | Time After Stage II Addition (min) | IV[A] | Composition[B] Polymer Mole % Glycolide | Residual Monomer Mole % Glycolide | Residual Monomer Mole % TMC | Average Segment Lengths[B] $Lt_n$ | $Lg_n$ | $Lg_w$ |
|---|---|---|---|---|---|---|---|---|---|
| 9A | Stage I | — | — | 13.8 | 0 | 3.6 | 3.81 | 1.12 | 1.21 |
| 9B | Stage II | 19 | 1.13 | 65.1 | 8.4 | 1.1 | 3.72 | 11.61 | 35.53 |
| 9C | Stage II | 24 | 1.26 | 67.0 | 2.2 | 1.2 | 3.77 | 14.14 | 39.39 |
| 9D | Stage II | 29 | 1.26 | 67.9 | 0.7 | 1.4 | 3.66 | 15.31 | 42.05 |
| 9E | Stage II | 34 | 1.22 | 67.6 | 0.5 | 1.1 | 3.49 | 14.03 | 38.36 |
| 9F | Stage II | 39 | 1.19 | 68.2 | 0.7 | — | 3.54 | 13.26 | 35.63 |
| 9G | Stage II | 44 | 1.09 | 67.9 | 0.6 | 0.8 | 3.55 | 13.13 | 37.33 |
| 9H | Stage II | 49 | 1.08 | 67.6 | 0.6 | 0.9 | 3.53 | 12.90 | 36.33 |

[A] 0.5 g/dL in Hexafluoroacetone sesquihydrate
[B] Determined on as-made copolymer by NMR analysis TABLE VI (b)

| Example | Thermal Properties[C] Tg (°C.)[D] | Tm (°C.)[E] | ΔHf (cal/g)[F] Total | ΔHf (cal/g)[G] High Melting Peak |
|---|---|---|---|---|
| 9A | — | — | — | — |
| 9B | — | — | — | — |
| 9C | −9.4, 36.7 | 217.2 | 11.68 | 11.00 |
| 9D | −9.7, 36.3 | 216.2 | 11.30 | 10.41 |
| 9E | −10.0, 34.3 | 215.5 | 11.62 | 10.69 |
| 9F | −9.9, 32.9 | 213.9 | 11.42 | 10.95 |
| 9G | 12.6 | 212.3 | 12.01 | 11.29 |
| 9H | 10.2 | 209.5 | 11.52 | 11.25 |

Figure 8:
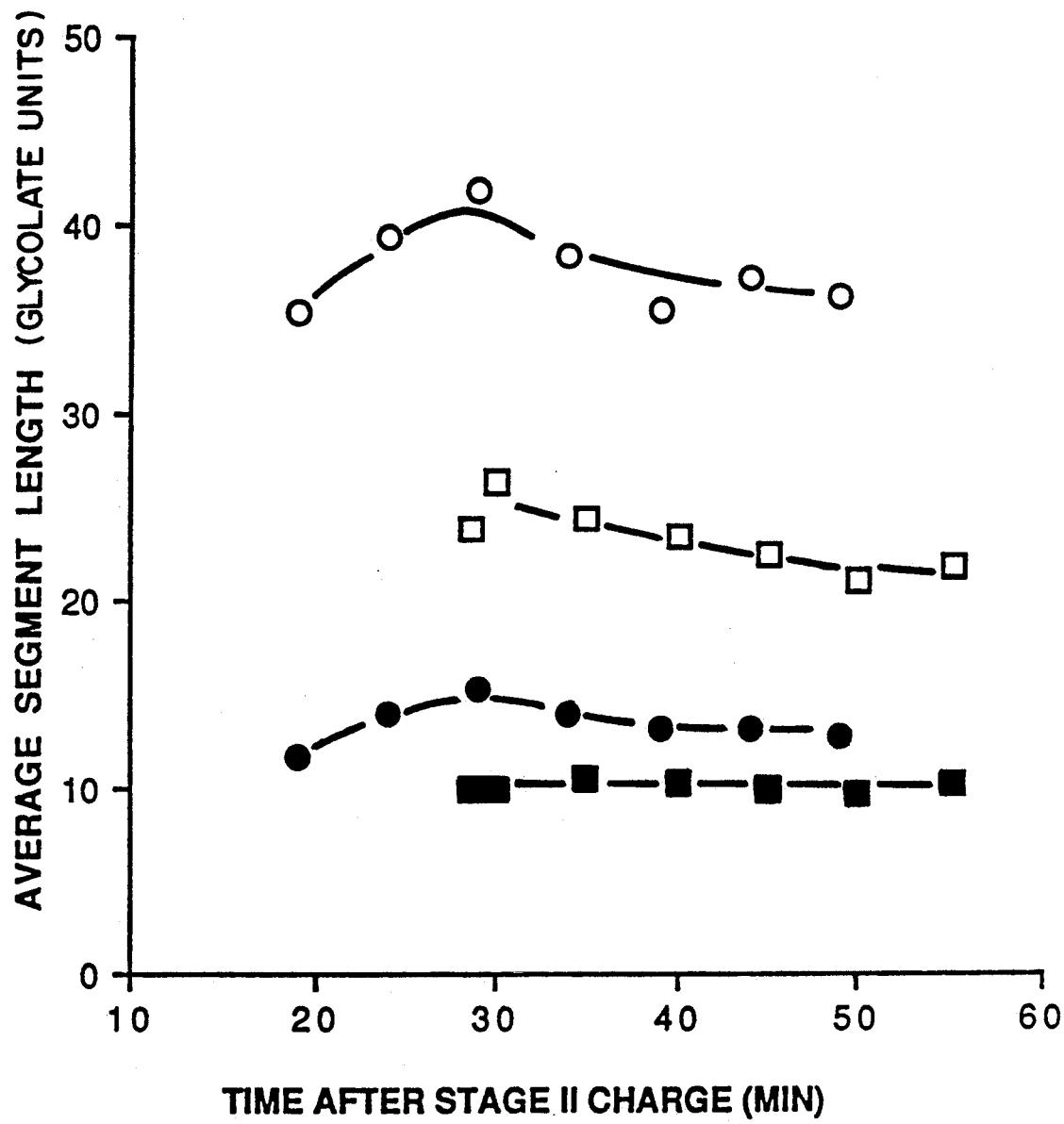
FIG. 8 shows the comparison of the average glycolate segment lengths ($Lg_n$ and $Lg_w$) for the copolymers of Examples 9 and 10.

[C] Determined on copolymer annealed at 110° C., <1 mm Hg overnight
[D] Temperature at midpoint of transition
[E] Temperature of melting peak maximum
[F] Measured over entire endotherm
[G] Measured over major high melting endotherm only $Lg_n$ and $Lt_n$ are relatively constant. However, $Lg_w$ decreases as a consequence of selective transesterification (see Table VII). In comparison to the two stage copolymer of Example 9, $Lt_n$ and $Lg_n$ are approximately the same. However, $Lg_w$ for the current example is markedly less than that of Example 9 (see FIG. 8). This is a consequence of the catalyst employed and its effect on the relative rates of transesterification and polymerization.

TABLE VII

| Ex. | Fraction | Time After Stage II Addition (min) | IV[A] | Composition[B] Polymer Mole % Glycolide | Residual Monomer Mole % Glycolide | Residual Monomer Mole % TMC | Average Segment Lengths[B] $Lt_n$ | $Lg_n$ | $Lg_w$ |
|---|---|---|---|---|---|---|---|---|---|
| 10A | Stage I | — | 1.73 | 14.7 | 0.1 | 4.1 | 3.52 | 1.22 | 1.46 |
| 10B | Stage II | 28 | 1.24 | 65.9 | 8.1 | 0.1 | 4.17 | 9.88 | 23.4 |
| 10C | Stage II | 30 | 1.26 | 68.3 | 3.3 | 1.2 | 3.39 | 10.05 | 26.54 |
| 10D | Stage II | 35 | 1.25 | 69.7 | 1.2 | 1.1 | 3.57 | 10.65 | 24.64 |
| 10E | Stage II | 40 | 1.21 | 68.7 | 0.6 | 1.0 | 3.29 | 10.34 | 23.59 |
| 10F | Stage II | 45 | 1.18 | 70.9 | 0.7 | 1.1 | 3.79 | 9.93 | 22.54 |
| 10G | Stage II | 50 | 1.14 | 70.2 | 1.2 | 0.8 | 3.56 | 9.74 | 21.30 |
| 10H | Stage II | 55 | 1.11 | 70.1 | 0.6 | 0.8 | 3.66 | 10.35 | 22.03 |

[A] 0.5 g/dL in Hexafluoroacetone sesquihydrate
[B] measured on as-made copolymer by NMR analysis

EXAMPLES 11-13

Preparation of Segmented Copolymers—Effect of Stage I Composition and Comparison of TMC and ε-caprolactone Three copolymers were prepared by a 2 stage copolymerization as outlined below (Table VIII). In each case the Stage I was prepared at 185° C. for 3 hours. The temperature was increased to 220° C. at which point the Stage II addition was made. Catalyst and initiator employed were stannous octoate (0.01 mole % based on total monomer) and lauryl alcohol (0.5 mole % based on total monomer) respectively. Samples were taken as noted in Table VIII.

Figure 9:
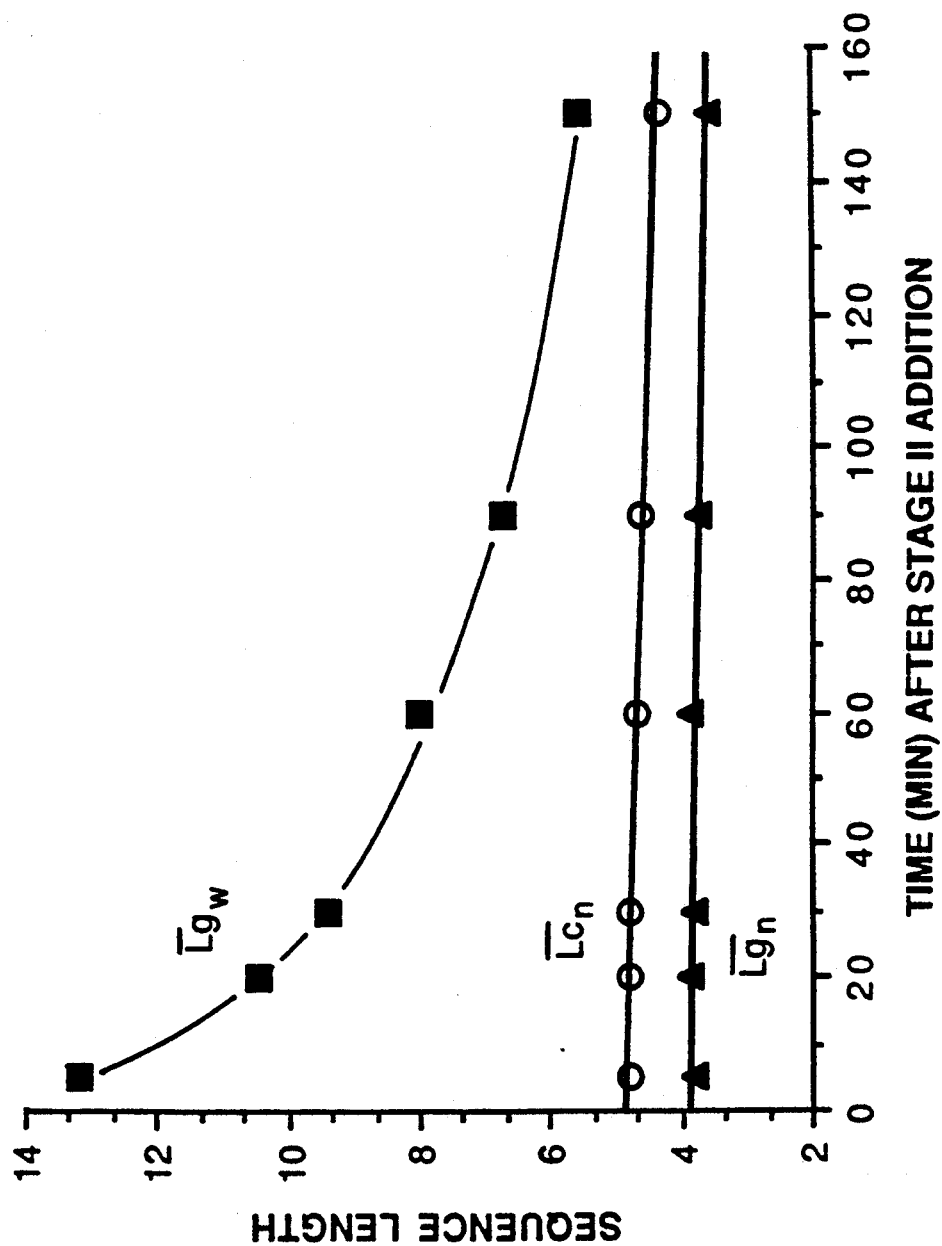
FIG. 9 shows in graphical form the various segment length values as a function of polymerization time, after the stage II addition, for the copolymers of Example 11.
Figure 10:
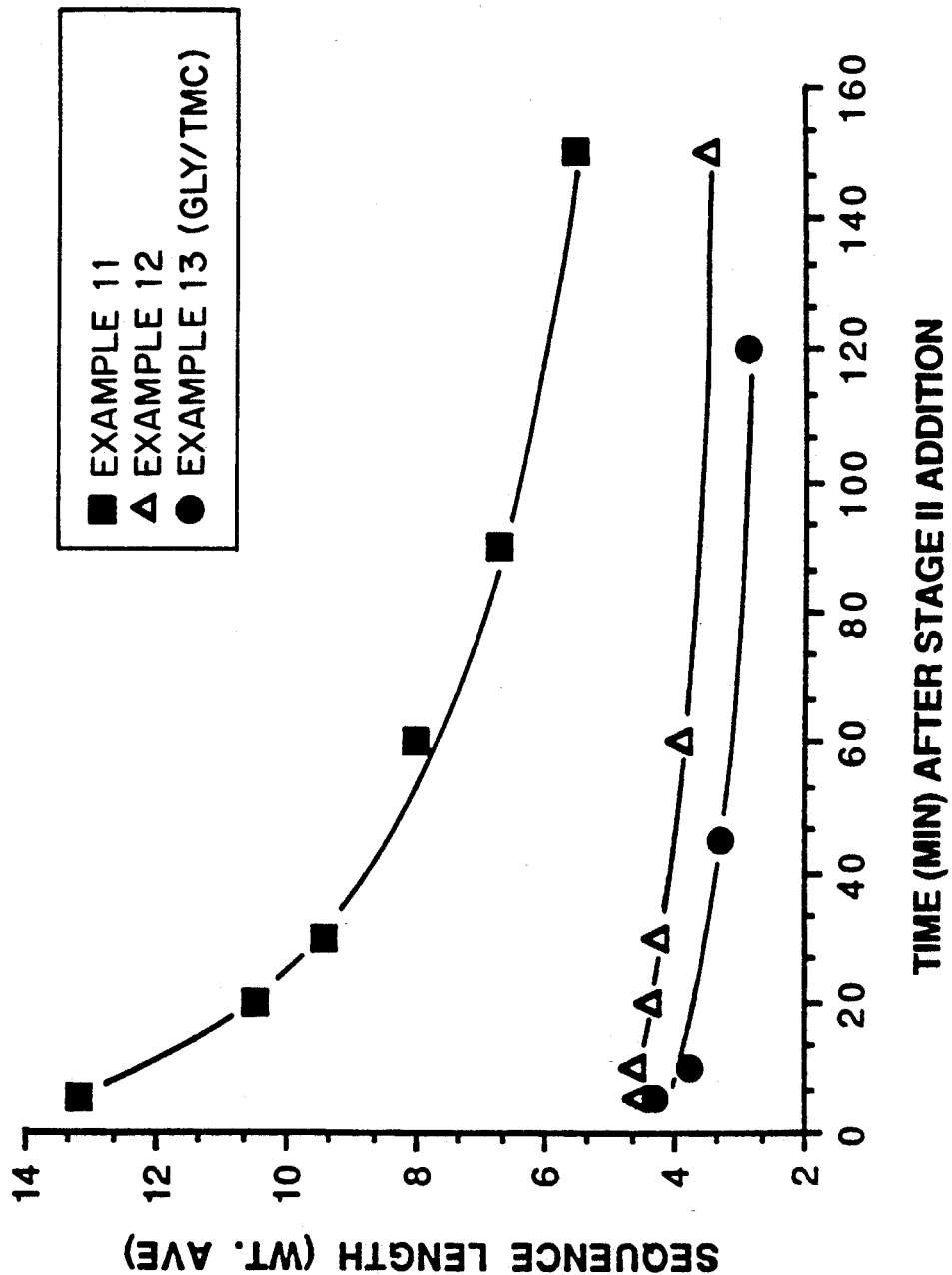
FIG. 10 shows in graphical form a comparison of the value of the weighted average glycolate segment length, $Lg_w$, for the copolymers of Examples 11, 12 and 13 as a function of polymerization time, after the stage II addition.

Average segment lengths for the copolymer of Example 11 are shown in FIG. 9. Both $Lc_n$ and $Lg_n$ are constant with time after Stage II addition, as noted in previous segmented copolymer examples (Examples 8 to 10). The weighted average segment length decreases with time after the Stage II addition as noted previously. These trends are also noted in the copolymers of Example 12 and Example 13. The effect of the first stage composition on final copolymer architecture is shown in FIG. 10. Increasing the concentration of the fast transesterifying glycolate linkages in the first stage results in a faster rate of transesterification and a markedly lower value of $Lg_w$, as illustrated by the difference between Examples 12 and 11. It should also be noted that ε-caprolactone and trimethylene carbonate behave similarly when employed in identical concentrations in the first stage, as evidenced by the values of $Lg_w$ for Example 12 and Example 13.

Figure 11:
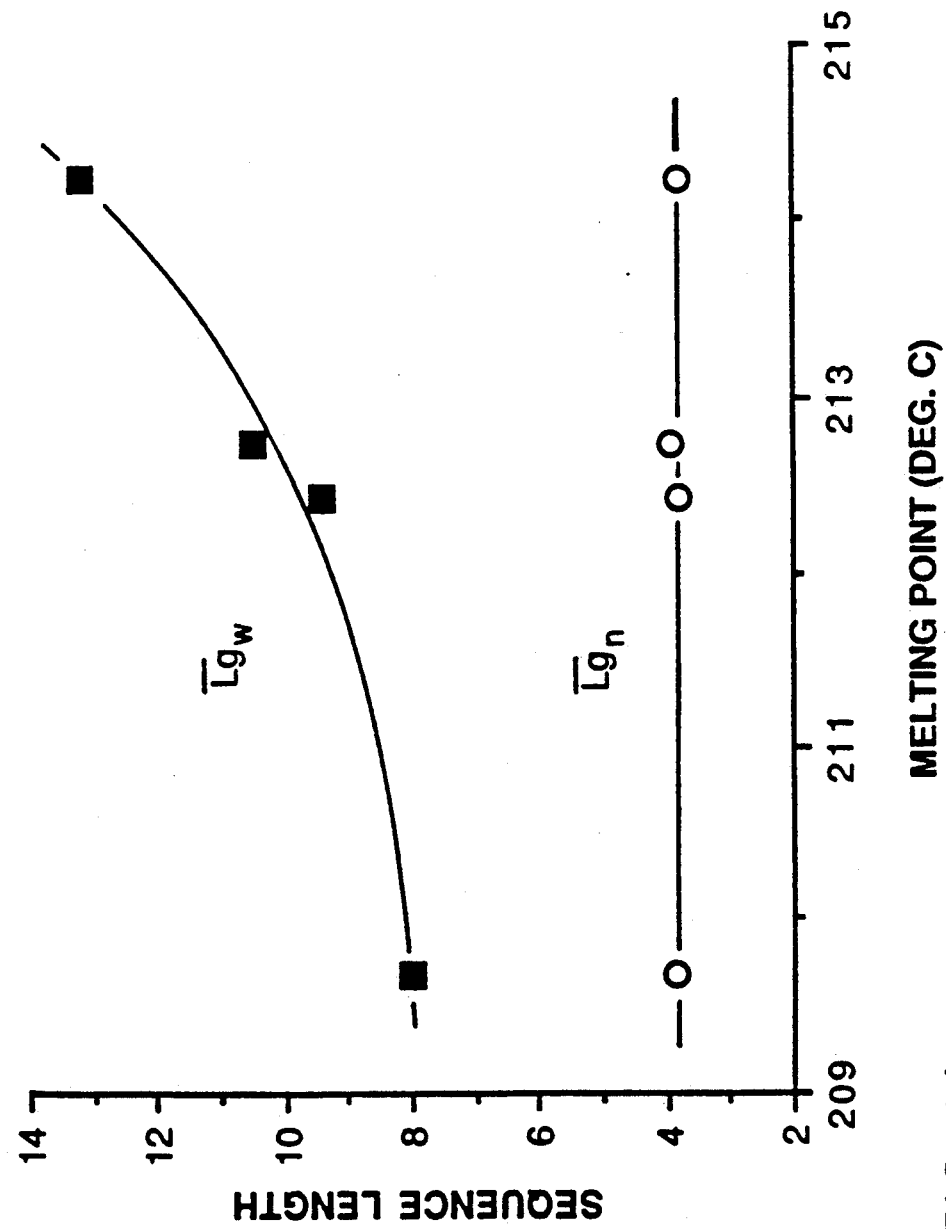
FIG. 11 shows in graphical form the relationship between melting point and the various glycolate segment lengths for the copolymer of Example 11.

The relationship between melting point and $Lg_w$ for Example 11 is shown in FIG. 11. No correlation is seen between $Lg_n$ and melting point, whereas a strong relationship is seen between $Lg_w$ and melting point, as also seen in Examples 8 through 10. As in previous cases a narrowing of the segment length distribution results in lower values for melting point and heat of fusion.

TABLE VIII

SEQUENTIAL ADDITION COPOLYMERIZATIONS

| | Example 11 CAP | Example 11 GLY | Example 12 CAP | Example 12 GLY | Example 13 TMC | Example 13 GLY |
|---|---|---|---|---|---|---|
| STAGE I | | | | | | |
| MOLES | 1.47 | 0.16 | 1.14 | 0.48 | 1.14 | 0.48 |
| MOLE % | 90 | 10 | 70 | 30 | 70 | 30 |
| STAGE II | | | | | | |
| MOLES | 0 | 0.46 | 0 | 0.46 | 0 | 0.46 |
| FINAL MOLE % | 70 | 30 | 55 | 45 | 55 | 45 |

SAMPLES TAKEN
STAGE I: 1, 2, 3 HRS
STAGE II: 5, 10, 20, 30, 45, 60, 75, 90, 105, 120, 150 MIN

EXAMPLES 14-19

Copolymers of L-lactide And Trimethylene Carbonate

A number of copolymers were prepared from l-lactide (l-Lac) and trimethylene carbonate (TMC) using a two stage reaction process (Table IX).

In Examples 14 to 17 the composition of the first stage was varied from 15 to 30 mole % l-Lac the remainder being TMC. The second stage was 100% l-Lac in all cases. The amount of TMC in Stage I was 0.64 moles and the amount of l-Lac in Stage II was 1.07 moles in all cases. Only the amount of l-Lac in Stage I was varied. In Example 18 the proportion of l-Lac in Stage II was increased by 50% compared to Example 16, otherwise it was a repeat of Example 16. In Example 19 the catalyst level was increased, otherwise it was a repeat of Example 15. The two stage method used to prepare these copolymers was as follows:

| | Stage I |
|---|---|
| Monomer charge: | |
| TMC: | 65.3 g (0.64 mol) |
| l-lac: | variable (see Table IX) |
| Catalyst: | Stannous octoate: 0.0013 mole % based on total monomer charged on both stages |
| Initiator: | Diethylene Glycol: 0.0113 mole % based on total monomer charged in both stages |
| Temperature: | 190° C. |
| Time: | 2 hours |
| | Stage II |
| Monomer Charge: | l-lac: 154.2 g (1.07 mol) |
| Temperature: | 190° C. |
| Time: | variable intervals (see Table X). |

Tensile specimens were injection molded using a CSI Mini-Max molder equipped with a 4 cc sample cup, and a standard CSI cylindrical dumbbell mold. In general the samples were heated in the sample cup to 20° C. above the melting temperature of the polymer prior to injection molding. The mold temperature was maintained at 80°-100° C. during the molding process. The mold was allowed to cool to approximately 50° C. prior to removal of the specimen. The molded specimens were annealed at 110° C. overnight under a dry nitrogen blanket prior to testing. Testing was carried out using a CSI tensile testing fixture and an Instron tensile testing machine.

Figure 12:
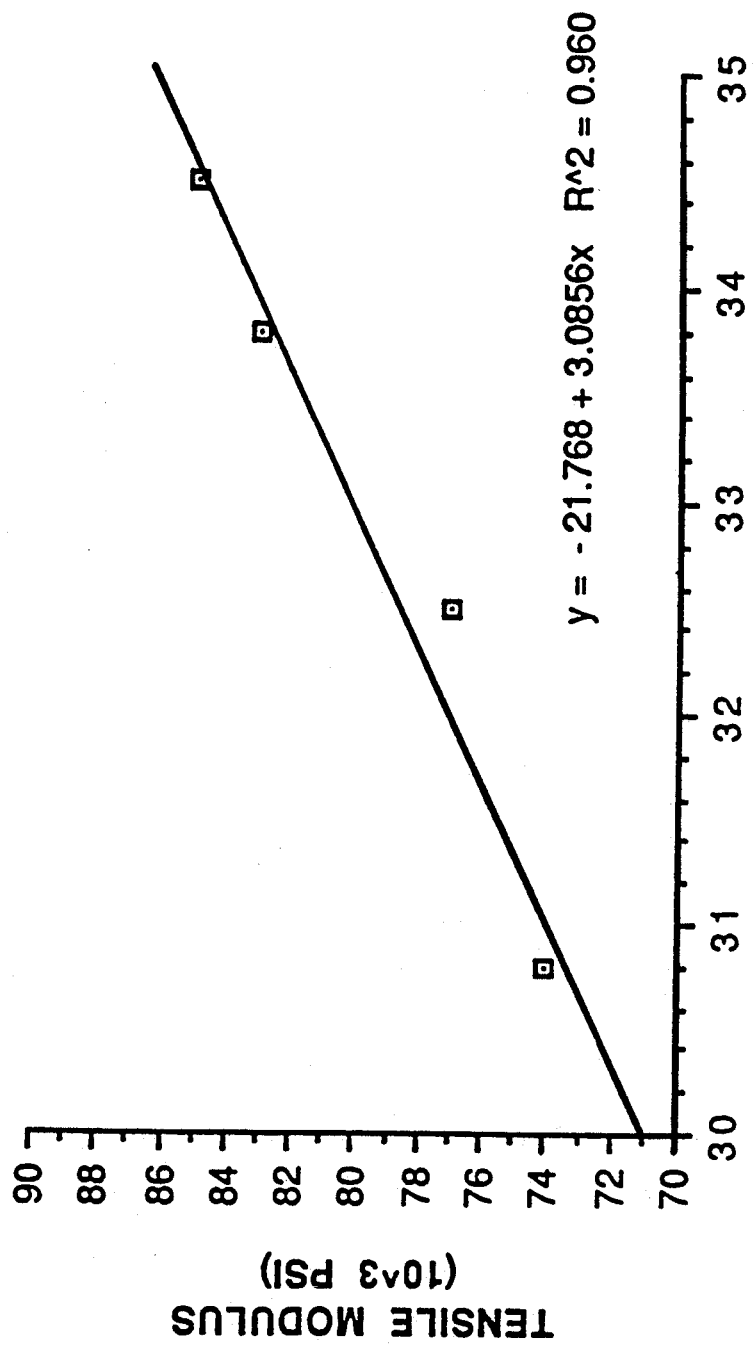
FIG. 12 shows in graphical form the correlation between tensile modulus and degree of crystallinity for the copolymers of Examples 14 to 19.

The mechanical properties of these materials appear to be linked to the overall crystallinity (see FIG. 12). Also, both modulus and crystallinity drop with increased 1-lactide content (see Table IX). For example, as one goes from Example 14 to 17 both the 1-lactide content in Stage I and overall 1-lactide or "hard segment" content increase, yet the modulus decreases. Furthermore, normalizing the crystallinity value for the weight fraction of Stage II shows a constant degree of crystallinity for the last stage of all the copolymers. These results indicate that little transesterification between the first and second stages has occurred and that good phase separation between the first and second stage blocks is maintained. The lack of extensive transesterification results in a broad segment length distribution. It is believed that below a certain critical segment length 1-lactide segments, which are normally considered hard segments, are not capable of crystallizing and therefore reside in the soft phase. It appears that linkages formed from lactide are slower to transesterify than linkages formed from glycolide in previously exemplified glycolide/trimethylene carbonate and glycolide/δ-caprolactone copolymers (Ex. 8–13). This could be due to the lower reaction temperature that is used for these lower melting point lactide copolymers. This slower rate gives added control over the architecture of the final lactide trimethylene carbonate copolymer. A more segmented architecture can be achieved by employing higher catalyst level in combination with longer reaction times. This is evidenced by comparison of examples 19a and 19b.

Figure 13:
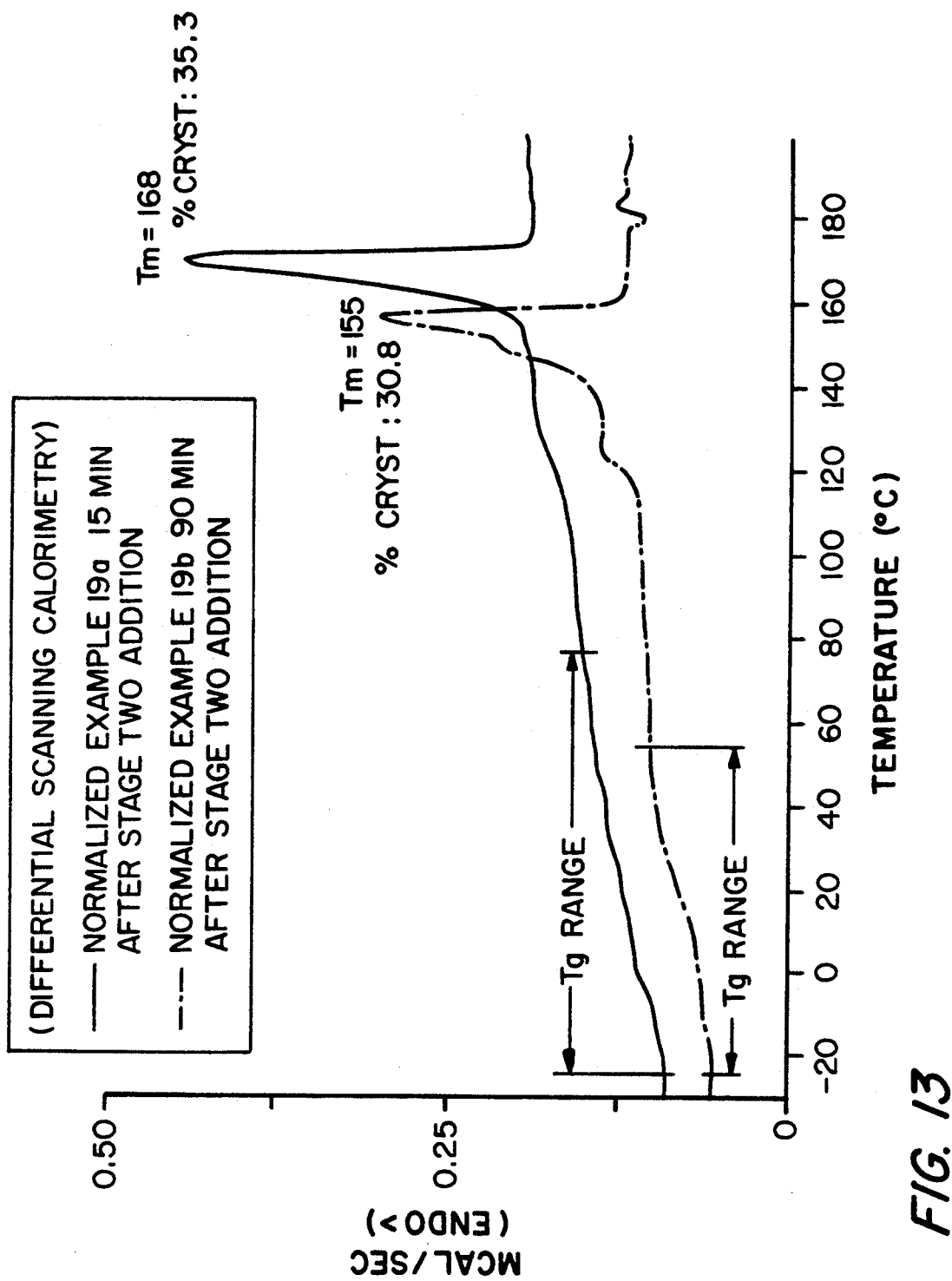
FIG. 13 shows two differential scanning calorimetry traces for the copolymers of Examples 19A and 19B.

In all cases the polymers were discharged in 20 g aliquots over various time intervals to determine the effect of transesterification on chain architecture and copolymer physical properties. The inherent viscosity (see Table X) is relatively stable over time, even for Example 19 which had an increased catalyst level. FIG. 13 shows thermal data for Example 19, 15 minutes after Stage II addition (Example 19a) and after 90 minutes (Example 19b). The shift of Tm and % crystallinity indicate morphology changes consistent with those observed in copolymers of glycolide and trimethylene carbonate (examples 8–10 and 13) or glycolide ε-caprolactone (examples 11 and 12) which have been shown to form segmented architectures.

TABLE X

IV Data for 1-lac/TMC Block Copolymers
IV in CHCl$_3$

| | Example: | | | | | |
|---|---|---|---|---|---|---|
| | 14 | 15 | 19[1] | 16 | 18[2] | 17 |
| l-lac/TMC (Stage I): | 5/95 | 13/87 | 13/87 | 20/80 | 20/80 | 30/70 |
| Stage I: | 1.30 | 0.83 | | 0.68 | 0.85 | 0.86 | 0.78 |
| Stage II Time[3] | | | | | | |
| 15 min | | | (19a) 1.12 | | | |
| 20 | | 0.60 | | | | |
| 25 | | 0.76 | | | | |
| 30 | 0.90 | 0.95 | | 1.06 | 1.19 | 0.66 |
| 35 | 1.01 | | | | | |
| 45 | | 1.24 | | 1.18 | 1.06 | |
| 60 | 1.42 | 1.38 | 1.04 | 1.39* | 1.29 | 0.98 |
| 75 | 1.51 | 1.40* | (19b) 1.05 | | | |
| 90 | 1.54 | 1.40 | | 1.35 | 1.45* | 1.08 |
| 105 | | 1.38 | | | | |
| 120 | 1.55* | 1.36 | 1.00 | 1.32 | 1.45 | 1.09* |
| 150 | 1.52 | 1.29 | 0.96 | 1.30 | 1.42 | 1.05 |
| 180 | 1.44 | | | | | |

[1] Repeat of Example 15 with higher catalyst conc.
[2] 50% more stage II than other samples
[3] Time (min) after addition of Stage II charge
*samples used for tensile testing

EXAMPLES 20–23

Monofilament Fibers From Copolymers Of Glycolide And Trimethylene Carbonate

Copolymers were prepared using a three stage copolymerization method. The intended overall chemical composition was the same for all of the copolymers in this series. Each stage of the polymerization was characterized by a monomer charge, a reaction time and a reaction temperature. The conditions for each reaction stage are shown in Table XI.

The four copolymers prepared in this example differed in the amount of glycolide monomer added to the reactor at each stage of the reaction. Table XII shows the specific amount (grams) of each comonomer used in each stage. The Examples described in Table XII were prepared in duplicate to check reproducibility and to obtain enough material for extrusion requirements. The analytical data for each of the duplicate batches are denoted in Table XIII by the example number suffixes a and b.

TABLE IX

1-Lactide/TMC Two Stage Copolymers
[Stage I is 1-Lactide/TMC random copolymer, Stage II is all 1-lactide]

| Exam.[1] ple # | IV CHCl$_3$ | Stage I[6] mol % l-lac | Stage I[6] L/T (moles) | % Crystallinity Total[4] | % Crystallinity Norm[4] | Tm °C. | Tg °C. | Tg range[5] Low | Tg range[5] High | Tensile Props Modulus (ksi) | Tensile Props Strength (break) (Ksi) |
|---|---|---|---|---|---|---|---|---|---|---|---|
| 14 | 1.55 | 63.3 | 5/95 | 34.5 | 50.1 | 169 | −10, 51 | −19 | 75 | 85 | 5.6 |
| 15 | 1.40 | 64.5 | 13/87 | 33.8 | 50.9 | 168 | 17 | −19 | 75 | 83 | 5.9 |
| 16 | 1.39 | 65.8 | 20/80 | 32.5 | 51.0 | 167 | 17 | −20 | 60 | 77 | 6.0 |
| 17 | 1.09 | 67.7 | 30/70 | 30.8 | 51.7 | 162 | 20 | −18 | 55 | 74 | 7.2 |
| 18[2] | 1.45 | 73.6 | 20/80 | 37.3 | 51.4 | 169 | 3 | −21 | 74 | | |
| 19a[3] | 1.12 | 64.5 | 13/87 | 35.3 | 53.2 | 168 | 9 | −21 | 75 | | |
| 19b[3] | 1.05 | 64.5 | 13/87 | 30.8 | 46.4 | 155 | 19 | −21 | 52 | | |

[1] All (except Ex. 19 series) were made using 0.0113 mole % Diethylene glycol initiator, and 0.0013 mole % stannous octoate catalyst, reaction temp. was 190° C.
[2] 50% more Stage II than Example 16.
[3] Repeat of Ex. 15, but with 0.01 mole % stannous octoate catalyst. Example 19a was removed 15 min. after Stage II charge, Example 19b was removed 90 min. after Stage II charge.
[4] Crystallinity determined by DSC using ΔH$_f$ of 22.4 cal/g for 100% crystalline poly(1-lactide). Normalized values are based on the weight fraction of Stage II only, rather than the total copolymer.
[5] Tg range represents the low and high temperatures of the Tg transition region.
[6] Mole % values are "as charged".

The copolymers were analyzed by $^1$H NMR for composition and residual monomer. The copolymer molecular weights were characterized by measuring the inherent viscosity (a solution of 0.5 g copolymer in 100 mL of hexafluoroacetone sesquihydrate, HFAS). The thermal properties were measured by Differential Scanning Calorimetry (DSC). The data from these measurements is shown in Table XIII. The inherent viscosities and compositions of these copolymers were all within a narrow range so that physical property differences cannot be associated with differences in these chemical properties.

The thermal data shown in Table XIII indicates a substantial decrease in melting temperature and a smaller drop in Enthalpy of Fusion from Examples 20 to 22. The weight percent of crystalline material in the solid copolymer can be calculated from the measured $\Delta H_f$ values using a $\alpha H_f$ value of 45.3 cal/g for 100% crystalline polyglycolide. Bee Polymer Handbook, 3rd Edition, J. Brandrup and E. Immergut eds., John Wiley & Sons, Inc., N.Y., 1989, which is incorporated herein by reference. These calculated crystallinity values are also shown in Table XIII.

The copolymer batches of the same number were combined to form one larger batch for extrusion (e.g. 20a and 20b were combined to form copolymer 20). The copolymers were extruded from a conventional 1 inch extruder at 217° C. into a room temperature water bath. They were then drawn into monofilaments with a draw ratio of about 7. The fibers were annealed under tension at 120° C. in vacuum for several hours. An Instron Tensile Tester was used to measure the resulting fiber properties. Table XIV shows the data from these tests. Both the modulus and the strength showed a substantial decrease from copolymer 20 to 23.

This is unexpected since the overall glycolate content (which would be expected to form hard segments) in the copolymers of Examples 20 through 23 are identical. However, the data is consistent with the segmented architectures described in Examples 8-19. As the concentration of fast reacting glycolate linkages in stage I is increased, the rate of subsequent reshuffling reactions is also increased. This leads to lower average segment lengths and to more narrow segment length distributions and results in less crystalline, lower melting, lower modulus and lower strength materials.

TABLE XI

| Stage I | |
|---|---|
| Monomer charge: | |
| TMC: | 81.2 g (0.796 mol) |
| Gly: | variable (see table XII). |
| Catalyst: | $SnCl_2 \cdot 2H_2O$: 5.9 mg (2.6 × 10$^{-5}$ mol) |
| Initiator: | Diethylene Glycol, 24.2 mg (2.3 × 10$^{-4}$ mol) |
| Temperature: | 180° C. |
| Time: | 2 hours |
| Stage II | |
| Monomer charge: | Gly: 23.2 g (0.199 mol) |
| Temperature: | charge at 180° C. then increase (1.5° C./min) to 195° C. |
| Time: | 30 min. |
| Stage III | |
| Monomer charge: | Gly: variable (see Table XII). |
| Temperature: | Charge at 195° C. then increase (1° C./min) to 215° C. |
| Time: | 20 to 30 min. Discharge at peak melt viscosity. |

TABLE XII

| Example | | Monomer Charges (in grams) | | | |
|---|---|---|---|---|---|
| | | Stage I | Stage II | Stage III | Total |
| 20 | TMC | 81.2 | — | — | 81.2 |
| | GLY | 14.3 | 23.2 | 131.3 | 168.8 |
| | TOTAL | 95.5 | 23.2 | 131.3 | 250.0 |
| 21 | TMC | 81.2 | — | — | 81.2 |
| | GLY | 27.1 | 23.2 | 118.5 | 168.8 |
| | TOTAL | 108.3 | 23.2 | 118.5 | 250.0 |
| 22 | TMC | 81.2 | — | — | 81.2 |
| | GLY | 43.8 | 23.2 | 101.8 | 168.8 |
| | TOTAL | 125.0 | 23.2 | 101.8 | 250.0 |
| 23 | TMC | 81.2 | — | — | 81.2 |
| | GLY | 66.4 | 23.2 | 79.2 | 168.8 |
| | TOTAL | 147.6 | 23.2 | 79.2 | 250.0 |

TABLE XIII

| Copolymer from Example | Analytical Data | | | | | | |
|---|---|---|---|---|---|---|---|
| | IV[1] dL/g | Wt % Gly[2] | Wt %[3] Monomer | Tm[4] °C. | $\Delta H_f$[5] cal/g | Tg[6] °C. | Cryst[7] % |
| 20a | 1.32 | 68.8 | 0.5 | 216 | 10.7 | 22.6 | 23.6 |
| 20b | 1.35 | 68.5 | 0.5 | 212 | 12.3 | 23.4 | 27.2 |
| 21a | 1.36 | 68.7 | 0.5 | 204 | 10.2 | 21.8 | 22.5 |
| 21b | 1.35 | 68.7 | 0.6 | 206 | 10.5 | 22.1 | 23.2 |
| 22a | 1.38 | 69.0 | 0.5 | 196 | 9.6 | 21.8 | 21.1 |
| 22b | 1.32 | 67.4 | 0.9 | 195 | 9.2 | 21.5 | 20.3 |
| 23a | 1.47 | 70.3 | 0.5 | 174 | 10.0 | 23.3 | 22.2 |
| 23b | 1.42 | 70.4 | 0.8 | 161 | 8.7 | 23.3 | 19.3 |

[1]0.5 g/dL in Hexafluoroacetone sesquihydrate (HFAS)
[2]overall wt. % glycolide in final copolymer determined by NMR
[3]wt % residual trimethylene carbonate monomer determined by NMR
[4]Temperature of melting peak maximum, measured on samples annealed in a vacuum oven at 110° C., <1 mm Hg overnight.
[5]determined by Differential Scanning Calorimetry
[6]Temperature at midpoint of transition
[7]($\Delta H_f$/45.3 cal/g) 100

TABLE XIV

| Copolymer from Example | Fiber Diam, mm | Fiber Data | | |
|---|---|---|---|---|
| | | TENSILE PROPERTIES | | |
| | | Strength PSI (× 10$^3$) | Modulus PSI (× 10$^3$) | Elongation At Break, % |
| 20 | 0.318 | 104.8 | 622 | 27.8 |
| 21 | 0.352 | 79.1 | 435 | 28.1 |
| 22 | 0.322 | 71.1 | 307 | 31.9 |
| 23 | 0.445 | 60.5 | 227 | 40.6 |

COMPARATIVE EXAMPLES 24–28

Statistical (or Random) Copolymers

Analytical data for a number of statistical copolymers of glycolide with trimethylene carbonate or glycolide with ε-caprolactone are shown in Table XV. Also included are a few previously described examples. Values of average segment length and segment length distribution are given. As the total glycolide in the copolymer is increased the number average glycolate segment length becomes larger. However, for these statistical copolymers the values of segment length distributions, (Lg$_w$/Lg$_n$) are narrow and are less than or equal to 1.25 across the entire composition range. In contrast, the copolymers of this invention all have segment length distributions of greater than 1.25. Also, it is evident that the slow slow transesterifying linkage must be present in excess of about 70 mole % to achieve a number average segment length greater than about 2.0. The ε-caprolactone and trimethylene carbonate appear to behave similarly when copolymerized with glycolide. This is exemplified by comparison of Example 11 (Stage 1) with Example 24, and Example 12 (Stage 1) and Example 3 with Example 13 (Stage 1).

TABLE XV

STATISTICAL COPOLYMERS - BLOCK LENGTHS AND BLOCK LENGTH DISTRIBUTIONS

| Sample Number | Monomers | Composition (moles %) | $Lg_n$ | $Lg_w$ | $Lg_w/Lg_n$ | $Lc_n$ (or $Lt_n$) |
|---|---|---|---|---|---|---|
| Ex 11 (Stage 1) | GLY/CAP | 10.3/90.7 | 1.14 | 1.26 | 1.10 | 4.88 |
| Ex 24 | GLY/TMC | 13.2/86.8 | 1.15 | 1.26 | 1.10 | 4.08 |
| Ex 12 (Stage 1) | GLY/CAP | 30.1/69.1 | 1.44 | 1.75 | 1.21 | 1.70 |
| Ex 3 | GLY/CAP | 31.2/68.8 | 1.46 | 1.77 | 1.21 | 1.58 |
| Ex 13 (Stage 1) | GLY/TMC | 32.6/67.4 | 1.57 | 1.92 | 1.22 | 1.76 |
| Ex 25 | GLY/TMC | 53.0/47.0 | 2.00 | 2.50 | 1.25 | 1.38 |
| Ex 26 | GLY/TMC | 67.7/32.3 | 6.38 | 7.39 | 1.16 | 1.74 |
| Ex 27 | GLY/TMC | 77.5/22.5 | 11.35 | 11.95 | 1.05 | 1.77 |
| Ex 28 | GLY/TMC | 94.3/5.7 | 48.48 | 53.44 | 1.10 | 2.18 |

What is claimed:

1. A copolymer comprising a bioabsorbable, segmented molecular architecture having at least two different ester linkages, the segmented molecular architecture comprising a plurality of fast transesterifying linkages having a segment length distribution of greater than 1.3, and a plurality of slow transesterifying linkages, with the proviso that for said fast transesterifying linkages consisting essentially of glycolate linkages and the slow transesterifying linkages selected from the group consisting of trimethylene carbonate and caproate linkages, the segment length distribution of said fast transesterifying linkages is up to 2.0 and the number average segment length of said slow transesterifying linkages is greater that 2.5 linkages per segment and with the further proviso that for said fast transesterifying linkages consisting essentially of lactate linkages and the slow transesterifying linkages selected from the group consisting of trimethylene carbonate linkages, the lactate linkages comprise greater than 60 to less than 80 mole percent of the copolymer.

2. The copolymer of claim 1 wherein said fast transesterifying linkages comprise lactate linkages.

3. The copolymer of claim 1 wherein said fast transesterifying linkages comprise glycolate linkages.

4. The copolymer of claim 1 wherein said fast transesterifying linkages comprise lactate and glycolate linkages.

5. The copolymer of claim 1 or 2 or 3 or 4 wherein the slow transesterifying linkages are selected from the group consisting of trimethylene carbonate, caproate and dioxanone linkages.

6. The copolymer of claim 1 or 2 or 3 or 4 wherein said slow transesterifying linkages comprise trimethylene carbonate linkages.

7. The copolymer of claim 1 or 2 or 3 or 4 wherein said slow transesterifying linkages comprise caproate linkages.

8. The copolymer of claim 2 wherein the lactate linkages have a crystallinity of less than about 40 percent based on differential scanning calorimetry and a melting point of less than about 170° C.

9. The copolymer of claim 3 wherein the glycolate linkages have a crystallinity of less than about 30 percent based on differential scanning calorimetry and a melting point of less than about 215° C.

10. A copolymer comprising a bioabsorbable, segmented molecular architecture having a plurality of lactate linkages, the segment length distribution of said lactate linkages being greater than 1.3, the crystallinity being less than about 40 percent based on differential scanning calorimetry and the melting point being less than about 170° C., and a plurality of trimethylene carbonate linkages, with the proviso that the lactate linkages comprise greater than 60 to less than 80 mole percent of the copolymer.

11. An article of manufacture selected from the group consisting of a molding resin, extrusion pellets, film and a controlled release device, each of the articles in said group comprising a copolymer, the copolymer having a bioabsorbable, synthetic, segmented molecular architecture, the segmented molecular architecture comprising a plurality of fast transesterifying linkages selected from the group consisting of lactate and glycolate linkages, and mixtures thereof, the fast transesterifying linkages having a segment length distribution of greater than 1.3, and a plurality of slow transesterifying linkages selected from the group consisting of trimethylene carbonate, caproate and dioxanone linkages, with the proviso that for said fast transesterifying linkages predominately comprising glycolate linkages and the slow transesterifying linkages selected from the group consisting of trimethylene carbonate and caproate linkages, the segment length distribution of said fast transesterifying linkages is up to 2.0 and the number average segment length of said slow transesterifying linkages is greater than 2.5 linkages per segment and with the further proviso that for said fast transesterifying linkages consisting essentially of lactate linkages and the slow transesterifying linkages selected from the group consisting of trimethylene carbonate linkages, the lactate linkages comprise greater than 60 to less than 80 mole percent of the copolymer.

12. The article of claim 11 wherein said fast transesterifying linkages comprise lactate linkages.

13. The article of claim 11 wherein said fast transesterifying linkages comprise glycolate linkages.

14. The article of claim 11 wherein said fast transesterifying linkages comprise lactate and glycolate linkages.

15. The article of claim 11 wherein said slow transesterifying linkages are selected from the group consisting of trimethylene carbonate and caproate linkages.

16. The article of claim 11 comprising a molding resin.

17. The article of claim 11 comprising extrusion pellets.

18. The article of claim 11 comprising a film.

19. An article comprising a sterile surgical element manufactured from a copolymer, the copolymer having a bioabsorbable, synthetic, segmented molecular architecture, the segmented molecular architecture comprising a plurality of fast transesterifying linkages selected from the group consisting of lactate and glycolate linkages, and mixtures thereof, the fast transesterifying linkages having a segment length distribution of greater than 1.3, and a plurality of slow transesterifying linkages selected from the group consisting of trimethylene carbonate, caproate and dioxanone linkages, with the proviso that for said fast transesterifying linkages predominately comprising glycolate linkages and the slow transesterifying linkages selected from the group consisting of trimethylene carbonate and caproate linkages, the segment length distribution of said fast transesterifying linkages is up to 2.0 and the number average segment length of said slow transesterifying linkages is greater than 2.5 linkages per segment and with the further proviso that for said fast transesterifying linkages consisting essentially of lactate linkages and the slow transesterifying linkages selected from the group consisting of trimethylene carbonate linkages, the lactate linkages comprise greater than 60 to less than 80 mole percent of the copolymer.

20. The article in any one of claims 12 to 15 or 19 wherein the sterile surgical element comprises at least one filament, the filament having a Young's modulus of from about 100,000 to 700,000 psi.

21. The article of claim 20 comprising a monofilament.

22. The article of claim 21 comprising a suture or ligature.

23. The article of claim 22 wherein the suture or ligature has a diameter of from about 0.02 to 0.70 mm; a Young's modulus of less than about 500,000 psi; a tensile strength of from about 50,000 to 150,000 psi; and an elongation to break of less than about 50 percent.

24. The article of claim 11 comprising a controlled release device.

25. The article of claim 24 comprising a plurality of microspheres.

26. The article of claim 24 in combination with a pharmaceutically or agronomically active ingredient.

27. The article of claim 24 in combination with a polypeptide or protein.

28. A process for manufacturing a copolymer having a bioabsorbable, segmented molecular architecture, the process comprising:
  employing sequential addition of at least two different cyclic ester monomers in at least two stages, the first cyclic ester monomer selected from the group consisting of carbonates and lactones, and mixtures thereof, and the second cyclic ester monomer selected from the group consisting of lactides and mixtures thereof, the sequential addition comprising:
  I. first polymerizing in a first stage at least said first cyclic ester monomer in the presence of a catalyst at a temperature of from about 160° to 220° C. to obtain a first polymer melt;
  II. adding at least said second cyclic ester monomer to the first polymer melt; and
  III. second copolymerizing in a second stage said first polymer melt with at least said second cyclic ester monomer to obtain a second copolymer melt; and
  transesterifying the second copolymer melt for up to about 5 hours at a temperature of greater than about 180° Centigrade.

29. The process of claim 28 wherein the employing substep I comprises first polymerizing in the first stage from about 80 mole percent of said first cyclic ester monomer, the remaining mole percentage, if any, comprising said second cyclic ester monomer.

30. The process of claim 29 wherein said employing substep I comprises first polymerizing in said first stage up to about 90 mole percent of said first cyclic ester monomer.

31. The process of claim 28 or 29 or 30 wherein the employing substep II comprises adding more than about 80 mole percent of said second cyclic ester monomer, the remaining mole percentage, if any, comprising said first cyclic ester monomer.

32. The process of claim 31 wherein said employing substep II comprises adding 100 mole percent of said second cyclic ester monomer.

33. A process for manufacturing a copolymer having a bioabsorbable, segmented molecular architecture, the process comprising:
  employing sequential addition of at least two different cyclic ester monomers in three stages, the first cyclic ester monomer selected from the group consisting of carbonates and lactones, and mixtures thereof, and the second cyclic ester monomer selected from the group consisting of lactides and mixtures thereof, the sequential addition comprising:
  I. first polymerizing in a first stage at least said first cyclic ester monomer in the presence of a catalyst at a temperature of from about 160° to 220° C. to obtain a first polymer melt;
  II. first adding at least said second cyclic ester monomer to the first polymer melt;
  III. second copolymerizing in a second stage said first polymer melt with at least said second cyclic ester monomer to obtain a second copolymer melt;
  IV. second adding at least said second cyclic ester monomer to the second copolymer melt; and
  V. third copolymerizing in a third stage said second copolymer melt with at least said second cyclic ester monomer to obtain a third copolymer melt; and
  transesterifying the third copolymer melt for up to about 5 hours at a temperature of greater than about greater than 180° centigrade.

34. The process of claim 33 wherein the employing substep I comprises first polymerizing in the first stage from about 80 mole percent of said first cyclic ester monomer, the remaining mole percentage, if any, comprising said second cyclic ester monomer.

35. The process of claim 34 wherein said employing substep I comprises first polymerizing in said first stage up to about 90 mole percent of said first cyclic ester monomer.

36. The process of claim 33 or 34 or 35 wherein the employing substeps II and/or IV comprise adding more than about 80 mole percent of said second cyclic ester monomer, the remaining mole percentage, if any, comprising said first cyclic ester monomer.

37. The process of claim 36 wherein said employing substeps II and/or IV comprise adding 100 mole percent of said second cyclic ester monomer.

38. The process of claim 28 or 30 or 33 or 35 wherein the employing step comprises polymerizing in the presence of a metal coordination catalyst.

39. The process of claim 28 or 30 or 33 or 35 wherein the employing step comprises polymerizing in the presence of an initiator.

40. The process of claim 39 wherein said employing step comprises polymerizing in the presence of an initiator selected from the group consisting of a monofunctional and polyfunctional alcohol.

* * * * *